US006902882B2

(12) United States Patent
Gu

(10) Patent No.: US 6,902,882 B2
(45) Date of Patent: Jun. 7, 2005

(54) METHODS OF MONITORING PRODUCTION OF GENE PRODUCTS AND USES THEREOF

(76) Inventor: Kerong Gu, 1965 Yearling Ct., Vienna, VA (US) 22182

( * ) Notice: Subject to any disclaimer, the term of this patent is extended or adjusted under 35 U.S.C. 154(b) by 55 days.

(21) Appl. No.: 09/859,155

(22) Filed: May 15, 2001

(65) Prior Publication Data

US 2002/0006605 A1 Jan. 17, 2002

Related U.S. Application Data

(60) Provisional application No. 60/207,523, filed on May 23, 2000.

(51) Int. Cl.$^7$ .................................................. C12Q 1/00
(52) U.S. Cl. ...................... 435/4; 435/320.1; 435/325; 435/455; 435/466; 435/468; 435/471; 435/483; 435/375
(58) Field of Search .............................. 800/3; 424/9.1; 435/375, 320.1, 325, 4, 7.21, 7.6, 8, 455, 466, 468, 471, 483

(56) References Cited

U.S. PATENT DOCUMENTS

| | | | |
|---|---|---|---|
| 4,981,754 A | 1/1991 | Hsu ............................ | 428/288 |
| 5,491,084 A | 2/1996 | Chalfie et al. ............... | 435/189 |
| 5,569,588 A | 10/1996 | Ashby et al. .................. | 435/6 |
| 5,777,079 A | 7/1998 | Tsien et al. .................. | 530/350 |
| 5,807,522 A | 9/1998 | Brown et al. .................. | 422/50 |
| 5,811,231 A | 9/1998 | Farr et al. ....................... | 435/6 |
| 5,955,280 A | 9/1999 | Vidal et al. ..................... | 435/6 |
| 5,965,352 A | 10/1999 | Stoughton et al. ............. | 435/4 |
| 5,965,368 A | 10/1999 | Vidal et al. ..................... | 435/6 |
| 5,968,738 A | 10/1999 | Anderson et al. .............. | 435/6 |
| 5,989,835 A | 11/1999 | Dunlay et al. ............... | 435/7.2 |
| 6,046,002 A | 4/2000 | Davis et al. ................... | 435/6 |
| 6,063,578 A * | 5/2000 | Barbosa et al. ................ | 435/6 |
| 6,410,013 B1 * | 6/2002 | Dong et al. ................. | 424/93.2 |

FOREIGN PATENT DOCUMENTS

| | | |
|---|---|---|
| WO | WO 94/17208 | 8/1994 |
| WO | WO 97/06277 | 2/1997 |

OTHER PUBLICATIONS

Blaney and Martin, Curr. Opin. Chem. Biol. (1997) 1(1):54–59.
Chee et al., Science (1996) 274:610–614.
Cubitt et al., Trends in Biochemical Sciences (1995) 20:448–455.
DeRisi et al., Nat. Genet. (1996) 14(4):457–460.
DeRisi et al., Science (1997) 278(5338):680–686.
Emr, Meth. Enzymol. (1990) 185:231.
Etcheverry, Meth. Enzymol. (1990) 185:319.
Fodor et al., Science (1991) 251:767–773.
Foury, Gene (1997) 195:1–10.
Gietz et al., Nucleic Acids Res. (1992) 20:1425.
Kingsmen et al., Meth. Enzymol. (1990) 185:329.
Kirsch, Curr. Opin. Biotechnol. (1993) 4(5):543–552.
Kozak, J. Biol. Chem. (1991) 266:19867–19870.
Lam, Anticancer Drug Des. (1997) 12:145–167.
Lashkari et al., Proc. Natl. Acad. Sci. USA (1997) 94(24):13057–13062.
Leeds et al., Mol. Cell. Biology (1992) 12:2165–2177.
Lipshutz et al., BioTechniques (1995) 19:442–447.
Mylin et al., Meth. Enzymol. (1990) 185:297.
Nacken et al., Gene (1996) 175:253.
Pease et al., Proc. Natl. Acad. Sci. USA (1994) 91:5022–5026.
Peters et al., Dev. Biol. (1995) 171:252–257.
Price et al., Meth. Enzymol. (1990).
Rine et al., Proc. Natl. Acad. Sci. USA (1983) 80:6750–6754.
Rizutto et al., Curr. Biol. (1995) 5:635–642.
Rose et al., Meth. Enzymol. (1990) 185:234.
Rosenberg et al., Meth. Enzymol. (1990) 185:341.
Rothstein et al., Meth. Enzymol. (1991) 194:281–301.
Schena et al., Meth. Enzymol. (1991) 194:389.
Schneider et al., Meth. Enzymol. (1991) 194:373.
Schultz and Schultz, Biotechnol. Prog. (1996) 12(6):729–743.
SenGupta et al., PNAS USA (1996) 93:8496–8501.
Shalon et al., Genome Res. (1996) 6:639.
Shoemaker et al., Nature Genetics (1996) 14:450.
Sledziewski, Meth. Enzymol. (1990) 185:351.
Stearns et al., Meth. Enzymol. (1990) 185:280.
Tietze and Lieb, Curr. Opin. Chem. Biol. (1998) 2(3):363–371.
Yang, T.–T., et al. (1998) *J of Biological Chemistry* 273(14):8212–8216.

* cited by examiner

*Primary Examiner*—Ram R. Shukla

(57) ABSTRACT

This invention relates generally to the field of monitoring production of gene products. In particular, the invention provides methods of monitoring production of a gene product, methods of screening for modulators of production of a gene product, and methods of screening for cellular targets amenable to regulation by a treatment using a plurality of reporter gene systems. The methods described herein find uses in a number of fields such as drug discovery, agricultural or industrial production and environmental monitoring or protection.

61 Claims, No Drawings

METHODS OF MONITORING PRODUCTION OF GENE PRODUCTS AND USES THEREOF

This application claims priority benefit of U.S. Provisional Patent Application Ser. No. 60/207,523, filed May 23, 2000, under 35 U.S.C. § 119(e). The disclosure of the above-described application is incorporated herein by reference in its entirety.

TECHNICAL FIELD

This invention relates generally to the field of monitoring production of gene products. In particular, the invention provides methods of monitoring production of a gene product, methods of screening for modulators of production of a gene product, and methods of screening for cellular targets amenable to regulation by a treatment using a plurality of reporter gene systems. The methods described herein find uses in a number of fields such as drug discovery, agricultural or industrial production and environmental monitoring or protection.

BACKGROUND ART

Methods for monitoring transcription or translation and their uses in drug screening are known in the art. For example, U.S. Pat. No. 5,811,231 discloses methods for measuring transcription or translation levels from genes linked to native eukaryotic stress promoters, especially those of mammals. The methods yield information concerning the action of a compound on a subcellular level which may be utilized to design antitoxins.

U.S. Pat. No. 5,569,588 discloses methods and compositions for estimating the physiological specificity of a candidate drug. The methods use one reporter in the cells and compare reporter gene product signals from each cells before and after contacting with candidate drug to obtain a drug response profile.

U.S. Pat. No. 5,965,352 discloses methods for determining the primary and secondary biological pathways through which a drug acts on a cell, and identifying the proteins and genes which are affected via each pathway. The method involves comparing measurements of RNA or protein abundances or activities in response to drug exposure with measurements of RNA or protein abundances or activities in pathways possibly affected by the drug in response to controlled, known perturbations of each pathway. Further, the invention provides methods for comparing the effects of two different drugs by comparing measurements of RNA or protein abundances in response to exposure to a first drug with RNA or protein abundances in response to exposure to another drug or drugs.

U.S. Pat. No. 6,046,002 discloses methods for identifying gene products that mediate a phenotype, such as drug resistance or sensitivity, as well as methods for identifying new bioactive compounds, by detecting differences in growth (e.g., as measured by growth rate) between host cells that differ in target gene product dosage (e.g., two copies of a target gene product-encoding sequence compared to one copy). Specifically, the invention features a method for identifying a nucleotide sequence encoding a target gene product of a bioactive compound by: a) culturing a first host cell and a second host cell in the presence of a bioactive compound, wherein the first host cell contains a target gene product-encoding sequence expressed at a first expression level, and the second host cell contains the target gene product-encoding sequence expressed at a second expression level, wherein the second expression level is less than the first expression level; and b) comparing growth rates of the first host cell and the second host cell. An alteration (e.g., increase or decrease) in growth rate of the second host cell relative to the growth rate of the first host cell indicates that the expression level of the candidate target gene product-encoding sequence is a determinant of resistance or sensitivity to the bioactive compound and the candidate target gene product-encoding sequence encodes a target gene product of the bioactive compound.

However, the above-described methods are based on one-reporter and two measuring points within these ranges, namely no exposure or perturbation and fully saturating exposure or perturbation, or one-reporter and perturbation strengths and drug exposure levels.

U.S. Pat. No. 5,807,522 discloses a method of detecting differential expression of each of a plurality of genes in a first cell type, with respect to expression of the same genes in a second cell type. In practicing the method, there is first produced fluorescent-labeled cDNAs from mRNAs isolated from the two cells types, where the cDNAs from the first and second cell types are labeled with first and second different fluorescent reporters. A mixture of the labeled cDNAs from the two cell types is added to an array of polynucleotides representing a plurality of known genes derived from the two cell types, under conditions that result in hybridization of the cDNAs to complementary-sequence polynucleotides in the array. The array is then examined by fluorescence under fluorescence excitation conditions in which (i) polynucleotides in the array that are hybridized predominantly to cDNAs derived from one of the first or second cell types give a distinct first or second fluorescence emission color, respectively, and (ii) polynucleotides in the array that are hybridized to substantially equal numbers of cDNAs derived from the first and second cell types give a distinct combined fluorescence emission color, respectively. The relative expression of known genes in the two cell types can then be determined by the observed fluorescence emission color of each spot. Obviously, this is a laborious procedure and very difficult to test thousands bioactive compounds with thousands different cells. Also there are discrepancies between duplicate experiment results, caused by multiple manipulating steps and technical limitations of DNA microarray technology. Therefore, there is still a need for an assay that has time and cost-saving features.

It would be desirable to have a screening method that are capable of screening large number, e.g., thousands, of drug candidates simultaneously and capable of providing accurate and reliable information about the actual target(s) of the drug or candidate drug. It would also be desirable to have a screening method that is fast and cost-effective. The present invention addresses these and other related needs in the art.

DISCLOSURE OF THE INVENTION

In one aspect, the present invention provides a method of screening for a modulator of production of a gene product, which method comprises: a) constructing a first host cell containing a first reporter gene operatively linked to a nucleotide sequence comprising at least the promoter portion of a target gene and constructing a second host cell containing a second reporter gene operatively linked to said nucleotide sequence to which said first reporter gene is linked, wherein expression of said first reporter gene results in a first detectable signal, expression of said second reporter gene results in a second detectable signal, said first and second detectable signals are distinct from each other but are integratable, and wherein mixing of said first and second host cells results in a third detectable signal distinct from said first and second detectable signals; b) detecting said third detectable signal from a mixture of said first and second host cells wherein neither type of said host cells is subjected to any desired treatment; c) detecting said third detectable signal from a mixture of said first and second host cells wherein one and only one type of said host cells is subjected to a desired treatment prior to said mixing of said host cells; and d) comparing said third detectable signals detected in steps b) and c), whereby said third detectable signal detected in step b) differs from that detected in step c) identifies said treatment as a modulator of production of said target gene product. Preferably, the method is used to screen for a modulator of production of a plurality of gene products. For example, in the above method, a first plurality of host cells can be constructed so that each of said first plurality of host cells contains a first reporter gene operatively linked to a different nucleotide sequence of a plurality of nucleotide sequences, a second plurality of host cells can be constructed so that each of said second plurality of host cells contains a second reporter gene operatively linked to a different nucleotide sequence of said plurality of nucleotide sequences to which said first reporter gene is linked in said first plurality host cells, and the method is used to identify a modulator of production of a plurality of gene products. More preferably, a plurality of treatments, e.g., test substances, can be screened against a plurality of target genes.

In another aspect, the present invention provides a method of screening for a cellular target amenable to regulation by a treatment, which method comprises: a) constructing a first host cell containing a first reporter gene operatively linked to a target nucleotide sequence and constructing a second host cell containing a second reporter gene operatively linked to said target nucleotide sequence to which said first reporter gene is linked, wherein expression of said first reporter gene results in a first detectable signal, expression of said second reporter gene results in a second detectable signal, said first and second detectable signals are distinct from each other but are integratable, and wherein mixing of said first and second host cells results in a third detectable signal distinct from said first and second detectable signals; b) detecting said third detectable signal from a mixture of said first and second host cells wherein neither type of said host cells is subjected to any desired treatment; c) detecting said third detectable signal from a mixture of said first and second host cells wherein one and only one type of said host cells is subjected to a desired treatment prior to said mixing of said host cells; and d) comparing said third detectable signals detected in steps b) and c), whereby said third detectable signal detected in step b) differs from that detected in step c) identifies said target nucleotide sequence as amenable to regulation by said treatment. Preferably, the method is used to screen for a plurality of cellular targets amenable to regulation by a treatment. For example, in the above method, a first plurality of host cells can be constructed so that each of said first plurality of host cells contains a first reporter gene operatively linked to a different target nucleotide sequence of a plurality of target nucleotide sequences, a second plurality of host cells can be constructed so that each of said second plurality of host cells contains a second reporter gene operatively linked to a different target nucleotide sequence of said plurality of target nucleotide sequences to which said first reporter gene is linked in said first plurality of host cells, and the method is used to identify at least one target nucleotide sequence within said plurality of target nucleotide sequences that is amenable to regulation by said treatment. More preferably, a plurality of cellular targets can be screened against a plurality of treatments, e.g., bioactive substances.

MODES OF CARRYING OUT THE INVENTION

The present invention provides methods of monitoring production of a gene product, methods of screening for modulators of production of a gene product, and methods of screening for cellular targets amenable to regulation by a treatment using a plurality of reporter gene systems. It is an objective of the present invention to provide a method for screening for bioactive compounds or drugs, or cellular targets, in single molecular or multiple component mixture using a multiple-color, e.g., two-color, global reporter system. It is another objective of the present invention to provide a method for screening for bioactive compounds or drugs, or cellular targets, in single molecular or multiple component that is fast, time and cost effective, and is readily adaptable to high throughput format. It is still another objective of the present invention to provide a method for screening for bioactive compounds or drugs, or cellular targets, in single molecular or multiple component avoiding the laborious procedures of extracting mRNA from cells. It is yet another objective of the present invention to provide a method for screening for bioactive compounds or drugs, or cellular targets, in single molecular or multiple component that can be conducted in vivo and can generate more sensitive and accurate mass amount of data in a time and cost effective manor. It is yet another objective of the present invention to provide a method for screening for bioactive compounds or drugs, or cellular targets, in single molecular or multiple component that is self-calibrating and that can measure any point or level or time of exposure without the two point or rang limitation and without the need of assessing the basal level in the assay.

A. Definitions

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails over the definition that is incorporated herein by reference.

As used herein, "a" or "an" means "at least one" or "one or more."

As used herein, "production of a gene product" refers to the entire process, and/or each or all steps involved in the process, of producing a final, function product from its encoding gene. The gene can be in the form of DNA or RNA sequences. The gene product can be in the form of nucleic acid that is complementary to the encoding gene or protein products encoded by the encoding gene. For example, if the encoding gene is a DNA sequence, the steps of the process can include, but are not limited to, expression of the gene by transcription into mRNA, translation of the mRNA into protein precursor, post-translational processing, modification to yield mature functional protein product, molecular transportation or secretion of the mature, functional protein product to the correct cellular or intercellular location, and metabolism of the encoding gene, the mRNA, the protein precursor or the mature, functional protein product.

As used herein, "modulator of production of a gene product" refers to any treatments (conditions) or substances that are capable of affecting, i.e., increasing or decreasing, production of a gene product. The modulator can affect production of a gene product through any mechanisms such as physical, chemical or biological mechanisms. Preferably, the modulator can be a test substance.

As used herein, "test substance" refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, or any combination of multiple components, etc.) whose effect on the production of a gene product is determined by the disclosed and/or claimed methods herein.

As used herein, "bioactive substance" refers to any substance that has been proven or suggested to have the ability of affecting a biological process or system. For example, any substance that are know to have prophylactic, therapeutic, prognostic or diagnostic value is considered a bioactive substance.

As used herein, "a cellular target amenable to regulation by a treatment" refers to the fact that the entire process, and/or each or all steps involved in the process, of producing a final, function product from its encoding gene is affected by the treatment (condition) or the substance.

As used herein, "a promoter portion" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated.

As used herein, "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, eg., Kozak, *J. Biol. Chem.*, 266:19867–19870 (1991)) can be inserted immediately 5' of the start codon and may enhance expression. The desirability of (or need for) such modification may be empirically determined.

As used herein, "detectable signal" means that the signal can be detected by any known detection means, including any physical, chemical or biological detection means.

As used herein, "distinct" signals means that the signals from the first and the second host cells and the signals from the mixture of the first and the second host cells can be distinguished by known detection means, including any physical, chemical or biological detection means.

As used herein, "integratable" signals means that the signals from the first and the second host cells can be integrated, i.e., combined, by known detection means, including any physical, chemical or biological detection means, to form the third detectable signal that is distinct from the first and the second detectable signal. The signals can be integratable because both signals are the same type of signals, e.g., both being fluorescent signals. Alternatively, although the signals are not the same type of signals, e.g., one being fluorescent an the other being radioactive, the signals can be manipulated, converted or quantified by the detection means so that the results generated by the manipulation, conversion or quantification are integratable.

As used herein, "plant" refers to any of various photosynthetic, eucaryotic multicellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

As used herein, "organ" refers to any part of the body exercising a specific function, as of respiration, secretion or digestion.

As used herein, "disease or disorder" refers to a pathological condition in an organism resulting from, e.g., infection or genetic defect, and characterized by identifiable symptoms.

As used herein, neoplasm (neoplasia) refers to abnormal new growth, and thus means the same as tumor, which may be benign or malignant. Unlike hyperplasia, neoplastic proliferation persists even in the absence of the original stimulus.

As used herein, cancer refers to a general term for diseases caused by any type of malignant tumor.

As used herein, "oncogene" refers to a mutated and/or overexpressed version of a normal gene of animal cells (the proto-oncogene) that in a dominant fashion can release the cell from normal restraints on growth, and thus alone, or in concert with other changes, convert a cell into a tumor cell. Exemplary oncogenes include, but are not limited to, abl, erba, erbB, ets, fes (fps), fgr, fms, fos, hst, int1, int2, jun, hit, B-lym, mas, met, mil (raf), mos, myb, myc, N-myc, neu (ErbB2), ral (mil), Ha-ras, Ki-ras, N-ras, rel, ros, sis, src, ski, trk and yes.

As used herein, "tumor suppressor gene" (or anti-oncogene, cancer susceptibility gene) refers to a gene that encodes a product which normally negatively regulates the cell cycle, and which must be mutated or otherwise inactivated before a cell can proceed to rapid division. Exemplary tumor suppressor genes include, but are not limited to, p16, p21, p53, RB (retinoblastoma), WT-1 (Wilm's tumor), DCC (deleted in colonic carcinoma), NF-1 (neurofibrosarcoma) and APC (adenomatous polypospis coli).

As used herein, "an immune system disease or disorder" refers to a pathological condition caused by a defect in the immune system. The immune system is a complex and highly developed system, yet its mission is simple: to seek and kill invaders. If a person is born with a severely defective immune system, death from infection by a virus, bacterium, fungus or parasite will occur. In severe combined immunodeficiency, lack of an enzyme means that toxic waste builds up inside immune system cells, killing them and thus devastating the immune system. A lack of immune system cells is also the basis for DiGeorge syndrome: improper development of the thymus gland means that T cell production is diminished. Most other immune disorders result from either an excessive immune response or an 'autoimmune attack'. For example, asthma, familial Mediterranean fever and Crohn disease (inflammatory bowel disease) all result from an over-reaction of the immune system, while autoimmune polyglandular syndrome and some facets of diabetes are due to the immune system attacking 'self' cells and molecules. A key part of the immune system's role is to differentiate between invaders and the body's own cells—when it fails to make this distinction, a reaction against 'self' cells and molecules causes autoimmune disease.

As used herein, "a metabolism disease or disorder" refers to a pathological condition caused by errors in metabolic processes. Metabolism is the means by which the body derives energy and synthesizes the other molecules it needs from the fats, carbohydrates and proteins we eat as food, by enzymatic reactions helped by minerals and vitamins. There is a significant level of tolerance of errors in the system: often, a mutation in one enzyme does not mean that the individual will suffer from a disease. A number of different enzymes may compete to modify the same molecule, and there may be more than one way to achieve the same end result for a variety of metabolic intermediates. Disease will only occur if a critical enzyme is disabled, or if a control mechanism for a metabolic pathway is affected.

As used herein, "a muscle and bone disease or disorder" refers to a pathological condition caused by defects in genes important for the formation and function of muscles, and connective tissues. Connective tissue is used herein as a broad term that includes bones, cartilage and tendons. For example, defects in fibrillin—a connective tissue protein that is important in making the tissue strong yet flexible—cause Marfan syndrome, while diastrophic dysplasia is caused by a defect in a sulfate transporter found in cartilage. Two diseases that originate through a defect in the muscle cells themselves are Duchenne muscular dystrophy (DMD) and myotonic dystrophy (DM). DM is another 'dynamic mutation' disease, similar to Huntington disease, that involves the expansion of a nucleotide repeat, this time in a muscle protein kinase gene. DMD involves a defect in the cytoskeletal protein, dystrophin, which is important for maintaining cell structure.

As used herein, "a nervous system disease or disorder" refers to a pathological condition caused by defects in the nervous system including the central nervous system, i.e., brain, and the peripheral nervous system. The brain and nervous system form an intricate network of electrical signals that are responsible for coordinating muscles, the senses, speech, memories, thought and emotion. Several diseases that directly affect the nervous system have a genetic component: some are due to a mutation in a single gene, others are proving to have a more complex mode of inheritance. As our understanding of the pathogenesis of neurodegenerative disorders deepens, common themes begin to emerge: Alzheimer brain plaques and the inclusion bodies found in Parkinson disease contain at least one common component, while Huntington disease, fragile X syndrome and spinocerebellar atrophy are all 'dynamic mutation' diseases in which there is an expansion of a DNA repeat sequence. Apoptosis is emerging as one of the molecular mechanisms invoked in several neurodegenerative diseases, as are other, specific, intracellular signaling events. The biosynthesis of myelin and the regulation of cholesterol traffic also figure in Charcot-Marie-Tooth and Neimann-Pick disease, respectively.

As used herein, "a signal disease or disorder" refers to a pathological condition caused by defects in the signal transduction process. Signal transduction within and between cells mean that they can communicate important information and act upon it. Hormones released from their site of synthesis carry a message to their target site, as in the case of leptin, which is released from adipose tissue (fat cells) and transported via the blood to the brain. Here, the leptin signals that enough has been eaten. Leptin binds to a receptor on the surface of hypothalamus cells, triggering subsequent intracellular signaling networks. Intracellular signaling defects account for several diseases, including cancers, ataxia telangiectasia and Cockayne syndrome. Faulty DNA repair mechanisms are also invoked in pathogenesis, since control of cell division, DNA synthesis and DNA repair all are inextricably linked. The end-result of many cell signals is to alter the expression of genes (transcription) by acting on DNA-binding proteins. Some diseases are the result of a lack of or a mutation in these proteins, which stop them from binding DNA in the normal way. Since signaling networks impinge on so many aspects of normal function, it is not surprising that so many diseases have at least some basis in a signaling defect.

As used herein, "a transporter disease or disorder" refers to a pathological condition caused by defects in a transporter, channel or pump. Transporters, channels or pumps that reside in cell membranes are key to maintaining the right balance of ions in cells, and are vital for transmitting signals from nerves to tissues. The consequences of defects in ion channels and transporters are diverse, depending on where they are located and what their cargo is. For example, in the heart, defects in potassium channels do not allow proper transmission of electrical impulses, resulting in the arrhythmia seen in long QT syndrome. In the lungs, failure of a sodium and chloride transporter found in epithelial cells leads to the congestion of cystic fibrosis, while one of the most common inherited forms of deafness, Pendred syndrome, looks to be associated with a defect in a sulphate transporter.

As used herein, "infection" refers to invasion of the body of a multi-cellular organism with organisms that have the potential to cause disease.

As used herein, "infectious organism" refers to an organism that is capable to cause infection of a multi-cellular organism. Most infectious organisms are microorganisms such as viruses, bacteria and fungi.

As used herein, "bacteria" refers to small prokaryotic organisms (linear dimensions of around 1 $\mu$m) with non-compartmentalized circular DNA and ribosomes of about 70S. Bacteria protein synthesis differs from that of eukaryotes. Many antibacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are 3 main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to obligate intracellular parasites of living but noncellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungi" refers to a division of eucaryotic organisms that grow in irregular masses, without roots, stems, or leaves, and are devoid of chlorophyll or other pigments capable of photosynthesis. Each organism (thallus) is unicellular to filamentous, and possess branched somatic structures (hyphae) surrounded by cell walls containing glucan or chitin or both, and containing true nuclei.

As used herein, "antibiotic" refers to a substance either derived from a mold or bacterium or organically synthesized, that inhibits the growth of certain microorganisms without substantially harming the host of the microorganisms to be killed or inhibited.

For clarity of disclosure, and not by way of limitation, the detailed description of the invention is divided into the subsections that follow.

B. Methods of Screening for Modulators of Production of Gene Products

In one aspect, the present invention provides a method of screening for a modulator of production of a gene product, which method comprises: a) constructing a first host cell containing a first reporter gene operatively linked to a nucleotide sequence comprising at least the promoter portion of a target gene and constructing a second host cell containing a second reporter gene operatively linked to said nucleotide sequence to which said first reporter gene is linked, wherein expression of said first reporter gene results in a first detectable signal, expression of said second reporter gene results in a second detectable signal, said first and second detectable signals are distinct from each other but are integratable, and wherein mixing of said first and second host cells results in a third detectable signal distinct from said first and second detectable signals; b) detecting said third detectable signal from a mixture of said first and second host cells wherein neither type of said host cells is subjected to any desired treatment; c) detecting said third detectable signal from a mixture of said first and second host cells wherein one and only one type of said host cells is subjected to a desired treatment prior to said mixing of said host cells; and d) comparing said third detectable signals detected in steps b) and c), whereby said third detectable signal detected in step b) differs from that detected in step c) identifies said treatment as a modulator of production of said target gene product.

The first and second host cells used in the method can have identical cell background. Alternatively, the first and second host cells used in the method can have different cell background. The method can be used in the "comparative genomic" studies. The first and second host cells can belong to two different species of the same or different genus. For example, the first and second host cells can be S. cerevisiae and S. pombe cells or S. cerevisiae and E.coli cells, respectively. In such settings, the methods can be used to identify modulators that modulates produciton of a gene product of the entire genus, e.g., yeast or microbe, or ones that only modulate produciton of a gene product of a particular species, e.g., S. cerevisiae, S. pombe or E.coli.

Any host cells, such as animal, plant, fungus, bacterium, viral infected or recombinant cells, can be used in the present methods. In one specific embodiment, the fungus cells used are yeast cells. Preferably, the yeast cells used are S. cerevisiae cells. In another specific embodiment, the animal cells used are fly, worm, insect or mammalian cells. Preferably, the mammalian cells used are human cells. The host cells used can be haploid or diploid cells. The host cells used can also contain a missense, a nonsense or a null mutation in at least one endogenous gene.

Any reporter genes can be used in the present methods. For example, reporter genes encoding enzymes or fluorescent proteins can be used. Exemplary enzymes include LacZ, CAT, invertase and phosphatase. The enzymes that affect fluorescence of a fluorescent substrate can also be used.

Any fluorescent proteins, i.e., fluorescent proteins of any color, can be used. Preferably, green, blue, red or yellow fluorescent proteins can be used. The green fluorescent protein (GFP) gene can be isolated from many organisms including jellyfish Aequorea victoria. The GFP gene encodes a protein which fluoresces when excited by violet or blue-green light. GFP is unique among reporters in that the GFP fluorophore spontaneously forms intracellularly without added cofactors, and in that it provides a direct readout of gene expression. In specific embodiments, GFPs disclosed in U.S. Pat. Nos. 5,491,084, 5,777,079 and 5,968,738 and GFPs disclosed in Peters et al., *Dev. Biol.*, 171:252–257 (1995), Rizzuto et al., *Curr. Biol,*. 5:635–642 (1995), and Cubitt et al., *Trends in Biochemical Sciences*, 20:448–455 (1995) can be used. In addition, commercially available fluorescent proteins such as Living Colors™ Red Fluorescent Protein (DsRed) (CLONTECH) can be used. This DsRed is isolated from the IndoPacific sea anemone relative Discosoma species. It has a vivid red fluorescence, making it ideal for multiple labeling. The DsRed fluoresces brightly with a maximum emission at 583 nm, red-shifted by more than 50 nm from the GFP and variant fluorescent proteins. This wavelength is easily detected using common rhodamine or propidium iodide filters. DsRed is efficiently excited by a 488-nm argon laser, making it well suited for use in flow cytometry or scanning confocal microscopy. For dual labeling with DsRed and EGFP a rhodamine or propidium iodide filter can be used to detect DsRed and a FITC filter or any EGFP-optimized filter can be used to detect EGFP. Cells can be triple-labeled if needed. New filter sets optimized for detecting DsRed are currently being developed by Omega Optical, Inc. and Chroma Technology Corp.

Other GFP, BFP and RFP can be used in the present methods. For instances, the green fluorescent proteins encoded by nucleic acids with the following GenBank accession Nos. can be used: U47949 (AGP1); U43284; AF007834 (GFPuv); U89686 (Saccharomyces cerevisiae synthetic green fluorescent protein (cox3::GFPm-3) gene); U89685 (Saccharomyces cerevisiae synthetic green fluorescent protein (cox3::GFPm) gene); U87974 (Synthetic construct modified green fluorescent protein GFP5-ER (mgfp5-ER)); U87973 (Synthetic construct modified green fluorescent protein GFP5 (mgfp5)); U87625 (Synthetic construct modified green fluorescent protein GFP-ER (mfgp4-ER)); U87624 (Synthetic construct green fluorescent protein (mgfp4) mRNA)); U73901 (Aequorea victoria mutant 3); U50963 (Synthetic); U70495 (soluble-modified green fluorescent protein (smGFP)); U57609 (enhanced green fluorescent protein gene); U57608 (enhanced green fluorescent protein gene); U57607 (enhanced green fluorescent protein gene); U57606 (enhanced green fluorescent protein gene); U55763 (enhanced green fluorescent protein (egfp); U55762 (enhanced green fluorescent protein (egfp); U55761 (enhanced green fluorescent protein (egfp); U54830 (Synthetic *E. coli* Tn3-derived transposon green fluorescent protein (GF); U36202; U36201; U19282; U19279; U19277; U19276; U19281; U19280; U19278; L29345 (Aequorea victoria); M62654 (Aequorea victoria); M62653 (Aequorea victoria); AAB47853 ((U87625) synthetic construct modified green fluorescent protein (GFP-ER)); AAB47852 ((U87624) synthetic construct green fluorescent protein).

Similarly, the blue fluorescent proteins encoded by nucleic acids with the following GenBank accession Nos. can be used: U70497 (soluble-modified blue fluorescent protein (smBFP); 1BFP (blue variant of green fluorescent protein); AAB16959 (soluble-modified blue fluorescent protein).

Also similarly, the red fluorescent proteins encoded by nucleic acids with the following GenBank accession Nos. can be used: U70496 (soluble-modified red-shifted green fluorescent protein (smRSGFP); AAB16958 (U70496) soluble-modified red-shifted green fluorescent protein).

Also similarly, the yellow fluorescent protein encoded by nucleic acid with the following GenBank accession No. can be used: M60852 (Vibrio fischeri yellow fluorescent protein (luxY) gene)).

The first and second reporter genes can encode different, but preferably same type of molecules. The reporter gene can further encode a molecular tag capable of identifying the host cell containing the reporter gene. Any substance capable of identifying the host cell can be used as the molecular tags. For example, the molecular tag can be a unique nucleotide sequence that can be recognized by a complementary nucleic acid sequence. The molecular tag can also be an unique protein that can be specifically recognized by an antibody, or vice verse.

Since "production of a gene product" refers to the entire process, and/or each or all steps involved in the process, of producing a final, function product from its encoding gene, the signal can be detected by detecting each, some or all steps or substances involved in the process. The signal detection can be based on the detection of quantity, expression kinetics, cellular location, transportation or metabolism of the product encoded by the reporter genes. For example, the signal can be detected by detecting mRNA encoded by the reporter gene. Alternatively, the signal can be detected by detecting protein encoded by the reporter gene.

The nucleotide sequence to which the reporter genes are linked can comprise only the promoter portion of the target gene. In addition, the nucleotide sequence can comprise the promoter portion and other transcriptional regulatory elements of the target gene. Moreover, the nucleotide sequence can comprise the promoter portion, other transcriptional regulatory elements and at least a portion of the coding sequence of the target gene. Preferably, the portion of the coding sequence of the target gene can direct post-translational protein processing, modification, cellular location, transportation or metabolism of the protein encoded by the target gene. Further, the nucleotide sequence can comprise the promoter portion, other transcriptional regulatory elements and entire coding sequence of the target gene. Finally, the nucleotide sequence can comprise the entire target gene. It is understood that when a reporter gene is linked to a nucleotide sequence comprising any portion of the coding sequence, e.g., protein coding sequence, the linking must be made in-frame.

The reporter gene operatively linked to the nucleotide sequence can be integrated into the genome of the host cell or can be maintained episomally in the host cell. For example, the reporter gene operatively linked to the nucleotide sequence can be maintained episomally in a plasmid in the host cell.

The first and second reporter genes can be expressed at the same or different levels. Such different expression levels of the first and second reporter genes can be caused by the different cell ploidities or by different copy numbers of the reporter genes contained in the host cells.

The nucleotide sequence can be endogenous or exogenous to the host cell. In one specific embodiment, the host cells used are yeast cells and the reporter genes are operatively linked to a nucleotide sequence of a non-yeast gene. Preferably, the yeast cells used are *S. cerevisiae* cells.

The host cells can be subjected to the treatment and the third detectable signals can be detected in vitro. Alternatively, the host cells can be derived from a multicellular organism, the host cells can be constructed and delivered to the multicellular organism, the host cells can be subjected to the treatment either in vitro before the delivery or in vivo after the delivery, and the third detectable signals can be detected in vivo. Preferably, the host cells are subjected to the treatment in vivo after the delivery, and the third detectable signals are detected in vivo.

Cells derived from any multicellular organism can be used. For example, cells from a transgenic animal are used.

The signals can be detected at any suitable time points or locations. Preferably, the signal detection is real-time and/or in-situ detection.

When the first host cell is treated, the third detectable signal detected in step c) moves toward the first detectable signal indicates that test substance enhances production of the target gene product controlled by the nucleotide sequence. Similarly, when the first host cell is treated, the third detectable signal detected in step c) moves toward the second detectable signal indicates that test substance inhibits production of said target gene product controlled by the nucleotide sequence. Analogous conclusion can be drawn when the second host cell is treated.

Any treatment including physical, e.g., light, fluorescent, luminescent or radioactive irradiation, temperature or concentration change, etc., chemical, e.g. pH change, or biological treatment, e.g., hormonal action, can be used in the present method. Preferably, the chemical treatment is effected by a test substance. In a preferred embodiment, a combinatorial library is used in the screening assays. Methods for synthesizing combinatorial libraries and characteristics of such combinatorial libraries are known in the art (*See generally, Combinatorial Libraries: Synthesis, Screening and Application Potential* (Cortese Ed.) Walter de Gruyter, Inc., 1995; Tietze and Lieb, *Curr. Opin. Chem. Biol.*, 2(3):363–71 (1998); Lam, *Anticancer Drug Des,.* 12(3):145–67 (1997); Blaney and Martin, *Curr. Opin. Chem. Biol.*, 1(1):54–9 (1997); and Schultz and Schultz, *Biotechnol. Prog,.* 12(6):729–43 (1996)).

Although the present method can be used to screen a single treatment or substance against a signal target gene, the method is preferably used in high throughput format, i.e., a plurality of treatments or substances is screened for simultaneously. More preferably, a plurality of treatments or substances is screened against a plurality of target genes simultaneously. For example, in the present method, a first plurality of host cells can be constructed so that each of said first plurality of host cells contains a first reporter gene operatively linked to a different nucleotide sequence of a plurality of nucleotide sequences, a second plurality of host cells can be constructed so that each of said second plurality of host cells contains a second reporter gene operatively linked to a different nucleotide sequence of said plurality of nucleotide sequences to which said first reporter gene is linked in said first plurality host cells, and the method can be used to identify a modulator of production of a plurality of gene products.

Preferably, the plurality of nucleotide sequences can be endogenous to the host cells and the host cells can be derived from a target organism. Also preferably, the plurality of nucleotide sequences comprises an ensemble of the transcriptional regulatory elements of the target organism sufficient to model the transcriptional responsiveness of the target organism to a treatment. More preferably, the ensemble comprises a majority of all different transcriptional regulatory elements of the target organism. For example, the ensemble can comprise a majority of all different transcriptional regulatory elements of a specific cellular stage, e.g., a specific stage in cell cycle, a specific cellular location, e.g., soluble or membrane bound, a specific cellular organelle, or a specific biochemical pathway, e.g., replication, transcription or translation, etc. Exemplary cellular organelles include nuclei, mitochondrion, chloroplast, ribosome, ER, Golgi apparatus, lysosome, proteasome, secretory vesicle, vacuole and microsome.

The target organism can be a multicellular organism and the ensemble can comprise a majority of all different transcriptional regulatory elements of a specific tissue or organ of the target organism. Exemplary tissues include connective, epithelium, muscle and nerve tissues. Exemplary organs include an accessory organ of the eye, annulospiral organ, auditory organ, Chievitz organ, circumventricular organ, Corti organ, critical organ, enamel organ, end organ, external female gential organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subformical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl. Preferably, the organ is an animal organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc.

The target organism can also be a multicellular organism and the ensemble comprises a majority of all different transcriptional regulatory elements of a specific developmentally stage of the target organism, such as fetus.

The ensemble can also be produced by duplicative genomewide insertions of first and second reporter genes. Such duplicative genomewide insertions of first and second reporter genes can be random or non-random insertions.

Any organism can be analyzed by the present methods. Preferably, mammals including humans or cells derived from humans can be analyzed by the present methods.

The target organism to be analyzed can be physiologically normal. The target organism to be analyzed can also be physiologically abnormal. For example, target organisms with diseses or disorders can be analyzed by the present methods. Exemplary diseases or disorders include cancers, immune system diseases or disorders, metabolism diseases or disorders, muscle and bone diseases or disorders, nervous system diseases or disorders, signal diseases or disorders, transporter diseases or disorders or infectious diseases. Such infectious diseases can be caused by infection by a fungus such as a yeast, a bacterium such as an eubacteria or an archaebacteria, or a virus such as a Class I virus, a Class II virus, a Class III virus, a Class IV virus, a Class V virus or a Class VI virus.

In a specific embodiment, more than two different reporter genes can be used in the present method.

In another specific embodiment, the first and second reporter genes can be used duplicatively as the reporter gene in a yeast two-hybrid system (see e.g., U.S. Pat. No. 5,283, 173), and the method is used for screening for a treatment that modulates the protein-protein interaction assessable by said yeast two-hybrid system. For example, a first yeast host cell can be constructed wherein a first reporter gene is under the control of the target promoter, which is activated by the joint action of an active domain (AD) and a binding domain (BD). A second yeast host cell can be constructed wherein a second reporter gene is under the control of the same target promoter, which is activated by the joint action of the AD and the BD. The first and the second reporter gene each has a distinct signal. The mixture of the first and the second host yeast cells in the absence of any test substance will result in a third signal distinct from the first and the second signal. If one of the host yeast cells is treated with a treatment or test substance and the treatment or test substance affects the protein-protein interaction detected by the yeast two-hybrid system, mixture of the first and second yeast host cells will cause a shift in the signal generated by such mixture, which in turn will indicate that the treatment or test substance affects the protein-protein interaction. The first and second reporter genes can similarly be used in other variations of the yeast two-hybrid system such as the reversed yeast two-hybrid system (see e.g., U.S. Pat. Nos. 5,965,368 and 5,955,280), the yeast one-hybrid system or the yeast three-hybrid system (SenGupta et al., *Genetics,* 93:8496–8501 (1996)).

C. Methods of Screening for Cellular Targets Amenable to Regulation by Treatments In another aspect, the present invention provides a method of screening for a cellular target amenable to regulation by a treatment, which method comprises: a) constructing a first host cell containing a first reporter gene operatively linked to a target nucleotide sequence and constructing a second host cell containing a second reporter gene operatively linked to said target nucleotide sequence to which said first reporter gene is linked, wherein expression of said first reporter gene results in a first detectable signal, expression of said second reporter gene results in a second detectable signal, said first and second detectable signals are distinct from each other but are integratable, and wherein mixing of said first and second host cells results in a third detectable signal distinct from said first and second detectable signals; b) detecting said third detectable signal from a mixture of said first and second host cells wherein neither type of said host cells is subjected to any desired treatment; c) detecting said third detectable signal from a mixture of said first and second host cells wherein one and only one type of said host cells is subjected to a desired treatment prior to said mixing of said host cells; and d) comparing said third detectable signals detected in steps b) and c), whereby said third detectable signal detected in step b) differs from that detected in step c) identifies said target nucleotide sequence as amenable to regulation by said treatment.

When the first host cell is treated, the third detectable signal detected in step c) moves toward the first detectable signal indicates that production of the gene product encoded by the target nucleotide sequence is up-regulated by the treatment. Similarly, when the first host cell is treated, the third detectable signal detected in step c) moves toward the second detectable signal indicates that production of the gene product encoded by the target nucleotide sequence is down-regulated by the treatment. Analogous conclusion can be drawn when the second host cell is treated. In this way, cellular targets amenable to regulation by a treatment(s) can be identified.

The treatment can be a physical, chemical or biological treatment. Preferably, the treatment is effected by a bioactive substance. For example, known antibiotics can be used to screen for cellular targets amenable to regulation, i.e., sensitive or resistant, to such antibiotics. Exemplary antibiotics include aminoglycosides (e.g., streptomycin, gentamicin, sisomicin, tobramycin, amicacin), ansamycins (e.g., rifamycin), antimycotics polyenes (e.g., nystatin, pimaricin, amphotericin B., pecilocin), benzofuran derivatives (e.g., griseofulvin), β-lactam antibiotics penicillins (e.g., penicillin G and its derivatives, oral penicillins, penicillinase-fixed penicillin broad-spectrum penicillins, penicillins active against *Proteus* and *Pseudomonas*), cephalosporins (e.g., cephalothin, cephaloridine, cephalexin, cefazolin, cefotaxime), chloramphenicol group (e.g., chloramphenicol, thiamphenicol, azidamphenicol), lmidazole fluconazole, itraconazole, linosamides (e.g., lincomycin, clindamycin), macrolides (e.g. azithromycin, erythromycin, oleandomycin, spiramycin, clarithromycin), peptides, peptolides, polypeptides (e.g., polymyxin B and E, bacitracin, tyrothricin, capreomycin, vancomycin), quinolones (e.g., nalidixic acid, ofloxacin, ciprofloxacin, norfioxin), tetracyclines (e.g., tetracycline, oxytetracycline, minocycline, doxycycline) and other antibiotics (e.g., phosphomycin, fusidic acid).

Preferably, in the above method, the target nucleotide sequence is screened against a plurality of treatments simultaneously. Also preferably, the target nucleotide sequence is screened against a plurality of bioactive substances simultaneously. More preferably, a plurality of target nucleotide sequences is screened against a plurality of treatments or bioactive substances simultaneously. For example, in the above method, a first plurality of host cells can be constructed so that each of said first plurality of host cells contains a first reporter gene operatively linked to a different target nucleotide sequence of a plurality of target nucleotide sequences, a second plurality of host cells can be constructed so that each of said second plurality of host cells contains a second reporter gene operatively linked to a different target nucleotide sequence of said plurality of target nucleotide sequences to which said first reporter gene is linked in said first plurality of host cells, and the method can be used to identify at least one target nucleotide sequence within said plurality of target nucleotide sequences that is amenable to regulation by said treatment.

The plurality of target nucleotide sequences can be endogenous to the host cells and the host cells can be derived from a target organism. Preferably, the plurality of target nucleotide sequences can comprise an ensemble of the transcriptional regulatory elements of the target organism sufficient to model the transcriptional responsiveness of the target organism to the treatment. More preferably, the ensemble can comprise a majority of all different transcriptional regulatory elements of the target organism.

In a specific embodiment, more than two different reporter genes can be used.

Host cells, reporter genes, detectable signals, signal detection means, target organisms, especially multicellular organisms, described in the above Section B can also be in the methods disclosed in this Section C. In addition, any variations disclosed and claimed in claims 2–57 can also be adapted and used in the method disclosed and claimed in claims 58–67.

D. Assays in Array Format

The methods disclosed in the above Sections B and C can be conducted in an array format on a solid surface, which is easily amenable to automation and high throughput screening procedures. For example, the first plurality of host cells, the second plurality of host cells, or the mixture of the first and second plurality of host cells can be placed and assayed in an array on a solid surface.

Preferably, the reporter genes used further comprise a molecular tag(s) to facilitate host cell identification. This feature is especially advantageous when the signal detection is based on the detection of mRNA encode by the reporter gene because this allows identification of a plurality of the mRNA molecules, e.g., by hybridization, in a single volume.

Any suitable solid surface can be used. For example, the solid surface can be silicon, plastic, glass, polymer, ceramic, photoresist and rubber surface. Exemplary polymers include cellulose, polyacrylamide, nylon, polystyrene, polyvinyl chloride and polypropylene. Preferably, the silicon surface is a silicon dioxide or a silicon nitride surface. Also preferably, the array is made in a chip format. Further preferably, the solid surfaces are in the form of tubes, beads, discs, silicon chips, microplates, polyvinylidene difluoride (PVDF) membrane, nitrocellulose membrane, nylon membrane, other purous membrane, non-porous membrane, a plurality of polymeric pins, or a plurality of microtitre wells.

As used herein, the word "array" means any ordered arrangement of a plurality of specified integers, including both liner and non-linear arrangements of a plurality of host cells. The array can be arranged on a grid, such as in microtitre wells, on a membrane support or silicon chip, or on a grid comprising a plurality of polymeric pins.

The cells can be attached to the solid surface by any methods known in the art. For example, the cells can be attached to the solid surface through cell surface molecule(s). The cells can be attached directly or through linker(s) to the surface. The cells can be attached to the surface through non-specific, specific, covalent, non-covalent, cleavable or non-cleavable linkage(s). The cleavable linkage can be cleavable upon physical, chemical or enzymatic treatment. The arrays can be arranged in any desired shapes such as linear, circular, etc.

Host cells, reporter genes, detectable signals, signal detection means, target organisms, especially multicellular organisms, described in the above Section B can also be in the methods disclosed in this Section D. In addition, any variations disclosed and claimed in claims 2–57 can also be adapted and used in the method disclosed and claimed in claims 68–76 and 82–83.

E. Methods of Monitoring Production of Gene Products

In still another aspect, the present invention provides a method of monitoring production of a gene product, which method comprises: a) constructing a first host cell containing a first reporter gene operatively linked to a nucleotide sequence comprising at least the promoter portion of a target gene and at least a portion of coding sequence of said target gene that directs production of said target gene product, and constructing a second host cell containing a second reporter gene operatively linked to said nucleotide sequence to which said first reporter gene is linked, wherein expression of said first reporter gene results in a first detectable signal, expression of said second reporter gene results in a second detectable signal, said first and second detectable signals are distinct from each other; b) detecting said first detectable signal; and c) detecting said second detectable signal, whereby production of said target gene product is monitored.

The production of the target gene product can be monitored by detecting quantity, expression kinetics, cellular location, transportation or metabolism of the product encoded by the reporter genes under the control of the nucleotide sequence of the target gene. Preferably, the production of the target gene product is monitored by detecting intracellular movement or cellular location of the product encoded by the reporter genes under the control of the nucleotide sequence of the target gene.

The method can further comprise subjecting one of the two host cells to a treatment and any alteration in production of the target gene product as identified by comparing the first and second detectable signals in the presence or absence of the treatment identifies that the treatment is capable of modulating production of the target gene product.

Host cells, reporter genes, detectable signals, signal detection means, target organisms, especially multicellular organisms, described in the above Section B can also be in the methods disclosed in this Section E. In addition, any variations disclosed and claimed in claims 2–57 can also be adapted and used in the method disclosed and claimed in claims 77–81.

F. Further Illustrations

The following description further illustrates certain characteristics and uses of the invention described in the above Sections B–E.

To maximize the reliability with which changes in gene expression levels could be discerned, we put one kind of reporter in each cells and another kind of reporter in exactly same cells as "reference". Then detecting differential expression of each of a plurality of genes in a first host cell, with respect to expression of the same genes in a second host cell "reference". In practicing the method, there is first produced two type fluorescent protein labeled same set cells, where the cells are transfected with or insert into genome with first and second different fluorescent protein reporters.

Specifically, the invention features a method for identifying the physiological specificity and for identifying gene products that mediate a phenotype to one or many bioactive compounds, the method comprising the steps of: a) culturing a first host cell and a second host cell in the presence or absence of a candidate bioactive compound; and b) capturing and determining the distribution, environment, or activity of fluorescently labeled reporter molecules in the first host cell and the second host cell separately; c) comparing the first host cell and the second host cell. An alteration (e.g., increase or decrease) of the second host cell relative to the first host cell indicates that the candidate bioactive compound has activity toward the target gene product and that the expression level of the candidate target gene product-encoding sequence is a determinant of resistance or sensitivity to the compound; d) mixture of the two cell types is added to an array. The array is then examined by fluorescence proteins in excitation conditions in which (i) the array that are mixed with one of the first or second host cell give a distinct first or second fluorescence protein emission color, respectively, and (ii) the array that are mixed with same treatment of the first and second cell types give a distinct combined fluorescence protein emission color, respectively. The relative expression of known genes in the two host cells can then be determined by the observed fluorescence protein emission color of each spot.

In still another aspect the inventions features a method for identifying a nucleotide sequence encoding a target gene product of a bioactive compound by: a) culturing a first host cell and a second host cell in the presence of a bioactive compound, wherein the first host cell contains a target gene product-encoding sequence expressed at a first expression level, and the second host cell contains the target gene product-encoding sequence expressed at a second expression level, wherein the second expression level is less than the first expression level; and b) comparing growth rates by measuring the strength of fluorescence protein emission of the first host cell and the second host cell. An alteration (e.g., increase or decrease) in growth rate of the second host cell relative to the growth rate of the first host cell indicates that the expression level of the candidate target gene product-encoding sequence is a determinant of resistance or sensitivity to the bioactive compound and the candidate target gene product-encoding sequence encodes a target gene product of the bioactive compound; c) mixture of the two cell types is added to an array. The array is then examined by fluorescence proteins in excitation conditions in which (i) the array that are mixed with one of the first or second host cell give a distinct first or second fluorescence protein emission color, respectively, and (ii) the array that are mixed with same treatment of the first and second cell types give a distinct combined fluorescence protein emission color, respectively. The relative expression of known genes in the two host cells can then be determined by the observed fluorescence protein emission color of each spot.

In still another aspect the inventions features a method for identifying a bioactive compound, the method comprising the steps of: a) culturing a first host cell and a second host cell in the presence of a candidate bioactive compound, wherein the first host cell contains a target gene product-encoding sequence expressed at a first expression level, and the second host cell contains the target gene product-encoding sequence expressed at a second expression level, wherein the second expression level is less than the first expression level; and b) comparing growth rate by measuring the strength of fluorescence protein emission of the first host cell and the second host cell. An alteration (e.g., increase or decrease) in growth rate of the second host cell relative to the growth rate of the first host cell indicates that the candidate bioactive compound has activity toward the target gene product and that the expression level of the candidate target gene product-encoding sequence is a determinant of resistance or sensitivity to the compound; c) mixture of the two cell types is added to an array. The array is then examined by fluorescence proteins in excitation conditions in which (i) the array that are mixed with one of the first or second host cell give a distinct first or second fluorescence protein emission color, respectively, and (ii) the array that are mixed with same treatment of the first and second cell types give a distinct combined fluorescence protein emission color, respectively. The relative expression of known genes in the two host cells can then be determined by the observed fluorescence protein emission color of each spot.

In another aspect the invention features a method for identifying a nucleotide sequence encoding a target gene product of a bioactive compound by: a) culturing a reference host cell and a heterozygous deletion host cell in the presence of a bioactive compound, where the reference host cell contains two copies of a target gene product-encoding sequence, and the heterozygous deletion host cell contains i) a site-specific deletion of the target gene product-encoding sequence, and ii) one functional copy of the target gene product-encoding sequence; and b) comparing the growth rates by measuring the strength of fluorescence protein emission of the reference host cell and the heterozygous deletion host cell. An alteration in growth rate (e.g., increase or decrease) of the heterozygous deletion host cell relative to growth rate of the reference host cell in the presence of the bioactive compound indicates that the heterozygous deletion strain contains a deletion in a target gene product-encoding sequence that encodes a target gene product of the bioactive compound; c) mixture of the two cell types is added to an array. The array is then examined by fluorescence proteins in excitation conditions in which (i) the array that are mixed with one of the first or second host cell give a distinct first or second fluorescence protein emission color, respectively, and (ii) the array that are mixed with same treatment of the first and second cell types give a distinct combined fluorescence protein emission color, respectively. The relative expression of known genes in the two host cells can then be determined by the observed fluorescence protein emission color of each spot.

In another aspect the invention features a method for identifying a bioactive compound by: a) culturing a reference host cell and a heterozygous deletion host cell in the presence of a candidate bioactive compound, where the reference host cell contains two copies of a target gene product-encoding sequence, and the heterozygous deletion host cell contains i) a site-specific deletion of the target gene product-encoding sequence, and ii) one functional copy of the target gene product-encoding sequence; and b) comparing growth rate by measuring the strength of fluorescence protein emission of the reference host cell and the heterozygous deletion host cell. An alteration in growth rate of the heterozygous deletion host cell relative to the growth rate of the reference host cell indicates that the candidate bioactive compound has activity toward the target gene product deleted in the heterozygous deletion strain; c) mixture of the two cell types is added to an array. The array is then examined by fluorescence proteins in excitation conditions in which (i) the array that are mixed with one of the first or second host cell give a distinct first or second fluorescence protein emission color, respectively, and (ii) the array that are mixed with same treatment of the first and second cell types give a distinct combined fluorescence protein emission color, respectively. The relative expression of known genes in the two host cells can then be determined by the observed fluorescence protein emission color of each spot.

In a preferred embodiment, the host cells contain molecular tags that uniquely identify each host cell in addition to the reporters. For example, where target gene expression in the second host cell is less than target gene expression in the first host cell, the first host cell contains a first molecular tag uniquely associated with the first host cell and the second host cell contains the same or a second molecular tag uniquely associated with the second host cell. Likewise, where the method uses reference and heterozygous deletion cells, the reference host cell contains a first molecular tag (preferably inserted into a non-functional gene), and the heterozygous deletion cell contains a second molecular tag that is uniquely associated with the site-specific deletion of the heterozygous deletion host cell. Where arrays are used, comparison of growth rates of the host cells (e.g., by assaying samples as a function of time) can be accomplished by: a) amplifying (e.g., by PCR) the first and second molecular tags to produce first and second amplified tags, b) hybridizing the amplified tags to an array of oligonucleotides including sequences of the first and second molecular tags; and c) comparing hybridization signals of the first and second molecular tags. An difference in the hybridization signal of the second molecular tag relative to the hybridization signal of the first molecular tag is indicative of an alteration in growth rate of the host cell containing the second molecular tag relative to the first host cell in the presence of the compound.

In another preferred embodiment, the host cells are grown in a single culture. Preferably, the host cells are yeast strains.

In yet another embodiment, where the reference host cell is a wildtype host cell, and the growth rate of the wildtype host cell is compared to the growth rates of two or more heterozygous deletion host cells, wherein each of the heterozygous deletion host cells contains a deletion in a different target gene product-encoding sequence.

In the most preferred embodiment, a mixture of the two cell types is added to an array. The array is then examined by fluorescence proteins in excitation conditions in which (i) the array that are mixed with one of the first or second cell types give a distinct first or second fluorescence protein emission color, respectively, and (ii) the array that are mixed with same treatment of the first and second cell types give a distinct combined fluorescence protein emission color, respectively. The relative expression of known genes in the two cell types can then be determined by the observed fluorescence protein emission color of each spot.

In this experimental design, the relative fluorescence protein intensity measured for the two reporters at each array element provides a reliable measure of the relative abundance of the corresponding mRNA and proteins in the two cell populations. Data from the series of thousands samples, consisting of more than thousands gene expression-ratio measurements, were organized into a database to facilitate efficient exploration and analysis of the results.

The global view of changes in expression of genes with known functions provides a vivid picture of the way in which the cell adapts to a changing environment. Just as the changes in expression of genes encoding pivotal enzymes can provide insight into metabolic reprogramming, the behavior of large groups of functionally related genes can provide a broad view of the systematic way in which the cell adapts to a changing environment. As more is learned about the functions of every gene in the organism genome, the ability to gain insight into a cell's response to a changing environment through its global gene expression patterns will become increasingly powerful.

Several distinct temporal patterns of expression could be recognized, and sets of genes could be grouped on the basis of the similarities in their expression patterns. The characterized members of each of these groups also shared important similarities in their functions. Moreover, in most cases, common regulatory mechanisms could be inferred for sets of genes with similar expression profiles.

Moreover, the differential expression measurements obtained by two color global reporter array are reproducible in duplicate experiments. For example, the remarkable changes in gene expression between the two kinds of cells mixed immediately after inoculation and immediately after the diauxic shift (the several intervals in this time series) are measured in duplicate, independently.

The changes in gene expression during this diauxic shift are complex and involve integration of many kinds of information about the nutritional and metabolic state of the cell. The large number of genes whose expression is altered and the diversity of temporal expression profiles observed in this experiment highlight the challenge of understanding the underlying regulatory mechanisms. One approach to defining the contributions of individual regulatory genes to a complex program of this kind is to use two color global reporter arrays to identify genes whose expression is affected by mutations in each putative regulatory gene. As a test of this strategy, we can analyze the genomewide changes in gene expression that result from deletion a specific gene.

Because the microarray allows us to monitor expression of nearly every gene in organism, we can, in principle, use this approach to identify all the transcriptional targets of a regulatory protein.

Use of the two color global reporter arrays to characterize the transcriptional and translational consequences of mutations affecting the activity of regulatory molecules provides a simple and powerful approach to dissection and characterization of regulatory pathways and networks. This strategy also has an important practical application in drug screening. Mutations in specific genes encoding candidate drug targets can serve as surrogates for the ideal chemical inhibitor or modulator of their activity. The two color global reporter arrays can be used to define the resulting signature pattern of alterations in gene expression, and then subsequently used in an assay to screen for compounds that reproduce the desired signature pattern.

The two color global reporter arrays provide a simple and economical way to explore gene expression patterns on a genomic scale. The equipment required for using two color global reporter arrays are commercially available. It was feasible for a small group to accomplish the construction of more than 6000 genes in about 4 months and, once the constructed cells are in hand, only 2 days are required to set up and generate of thousands results of 6400 elements each. Medium preparation, inoculation, and fluorescent protein imaging are also simple procedures. Even conceptually simple experiments can yield vast amounts of information. The value of the information from each experiment of this kind will progressively increase as more is learned about the functions of each gene and as additional experiments define the global changes in gene expression in diverse other natural processes and genetic perturbations.

The Variation of the Two Color Global Reporter Arrays
1) Construct two reporters in exactly same genetic and equal cell background, monitoring them, beside the drug or bioactive compound, in the same conditions,
2) The construct also can be in unequal cell background, such as over-expression form,
3) The two reporters are also in plasmid instead genome insert,
4) The copy number of the reporters can be control to test the drug effect, such as haploid and diploid,
5) The host cell can be in a deletion background,
6) The reporters can be added of molecular tag for the convenience to monitor the mRNA level by array or chip technology,
7) The two color reporter array are limited in two color, can be multiple color or kind reporters, such as CAT, LacZ et al. The two color is for illustration only,
8) This system can identify multiple targets or pathways or global genomic level of a drug effect,
9) This system can identify multiple targets or pathways or global genomic level of multiple compound or mixture (instead pure agent) effect,
10) This system can identify multiple targets or pathways or global genomic level of chemical compounds or unpurified mixture and also natural products effect,
11) This system take advantage of the available genomic information,
12) This system does not need to know the gene function or pathway, an function or pathway unknown genes data still can be readily attained
13) This system can use the compare genomics to discovery new drug, such as specific antifungi and general antifungi drugs,
14) This system can identification of new drug for known drug and new drug alike,
15) This system can finding the pathways of the drug effect,
16) This system have high sensitivities to all genes, not simple negative or positive to single gene or enzyme or a pathway,
17) This system can adapt to high throughput or high density array or chips,
18) The process time very faster, just hours and days,
19) It is a very inexpensive way to screening new drug or monitoring bioactive compounds effect,
20) Once a target of a known drug in the database, it is very easy to find other new drug,
21) It can in vary kinds of host cells, haploid or diploid, bacteria, yeast, fungi, fly, worm, plant, mammalian cells, et al.
22) It can be use in transgenics animal model too,
23) This system can be use to monitoring real time gene expression and gene products accumulation and degradation,
24) This system can be use to monitor real time gene products localization and distribution or metabolize,
25) This system can be integrate with yeast two hybrid methods to monitoring gene products that belong to other cells, Advantages of the Two Color Global Reporter Arrays as a Vehicle for Pharmaceutical Development The advantages of the subject methods over prior art drug screening methods may be illustrated by examples. Consider the difference between an in vitro assay for HMG-CoA reductase inhibitors as presently practiced by the pharmaceutical industry, and an assay for inhibitors of sterol biosynthesis as revealed by the ERG 10 reporter. In the case of the former, information is obtained only for those rare compounds that happen to inhibit this one enzyme. In contrast, in the case of the ERG 10 reporter, any compound that inhibits nearly any of the approximately 35 steps in the sterol biosynthetic pathway will, by lowering the level of intracellular sterols, induce the synthesis of the reporter. Thus, the reporter can detect a much broader range of targets than can the purified enzyme, in this case 35 times more than the in vitro assay.

Drugs often have side effects that are in part due to the lack of target specificity. However, the in vitro assay of HMG-CoA reductase provides no information on the specificity of a compound. In contrast, a genome reporter matrix reveals the spectrum of other genes in the genome also affected by the compound. In considering two different compounds both of which induce the ERG10 reporter, if one compound affects the expression of 5 other reporters and a second compound affects the expression of 50 other reporters, the first compound is, a priori, more likely to have fewer side effects. Because the identity of the reporters is known or determinable, information on other affected reporters is informative as to the nature of the side effect. A panel of reporters can be used to test derivatives of the lead compound to determine which of the derivatives have greater specificity than the first compound.

As another example, consider the case of a compound that does not affect the in vitro assay for HMG-CoA reductase nor induces the expression of the ERG10 reporter. In the traditional approach to drug discovery, a compound that does not inhibit the target being tested provides no useful information. However, a compound having any significant effect on a biological process generally has some consequence on gene expression. A genome reporter matrix can thus provide two different kinds of information for most compounds. In some cases, the identity of reporter genes affected by the inhibitor evidences how the inhibitor functions. For example, a compound that induces a cAMP-dependent promoter in yeast may affect the activity of the Ras pathway. Even where the compound affects the expression of a set of genes that do not evidence the action of the compound, the matrix provides a comprehensive assessment of the action of the compound that can be stored in a database for later analyses. A library of such matrix response profiles can be continuously investigated, much as the Spectral Compendiums of chemistry are continually referenced in the chemical arts. For example, if the database reveals that compound X alters the expression of gene Y, and a paper is published reporting that the expression of gene Y is sensitive to, for example, the inositol phosphate signaling pathway, compound X is a candidate for modulating the inositol phosphate signaling pathway. In effect the genome reporter matrix is an informational translator that takes information on a gene directly to a compound that may already have been found to affect the expression of that gene. This tool should dramatically shorten the research and discovery phase of drug development, and effectively leverage the value of the publicly available research portfolio on all genes.

In many cases, a drug of interest would work on protein targets whose impact on gene expression would not be known a priori. The genome reporter matrix can nevertheless be used to estimate which genes would be induced or repressed by the drug. In one embodiment, a dominant mutant form of the gene encoding a drug-targeted protein is introduced into all the strains of the genome reporter matrix and the effect of the dominant mutant, which interferes with the gene product's normal function, evaluated for each reporter. This genetic assay informs us which genes would be affected by a drug that has a similar mechanism of action. In many cases, the drug itself could be used to obtain the same information. However, even if the drug itself were not available, genetics can be used to predetermine what its response profile would be in the genome reporter matrix. Furthermore, it is not necessary to know the identity of any of the responding genes. Instead, the genetic control with the dominant mutant sorts the genome into those genes that respond and those that do not. Hence, if drugs that disrupt a given cellular function were desired, dominant mutants for such function introduced into the genome reporter matrix reveal what response profile to expect for such an agent.

For example, taxol, a recent advance in potential breast cancer therapies, has been shown to interfere with tubulin-based cytoskeletal elements. Hence, a dominant mutant form of tubulin provides a response profile informative for breast cancer therapies with similar modes of action to taxol. Specifically, a dominant mutant form of tubulin is introduced into all the strains of the genome reporter matrix and the effect of this dominant mutant, which interferes with the microtubule cytoskeleton, evaluated for each reporter. Thus, any new compound that induces the same response profile as the dominant tubulin mutant would provide a candidate for a taxol-like pharmaceutical.

In addition, the genome reporter matrix can be used to genetically create or model various disease states. In this way, pathways present specifically in the disease state can be targeted. For example, the specific response profile of transforming mutant $Ras^2val19$ identifies $Ras^2val19$ induced reporters. Here, the matrix, in which each unit contains the $Ras^2val19$ mutation is used to screen for compounds that restore the response profile to that of the matrix lacking the mutation.

Though these examples are directed to the development of human therapeutics, informative response profiles can often be obtained in nonhuman reporter matrices. Hence, for disease causing genes with yeast homologs, even if the function of the gene is not known, a dominant form of the gene can be introduced into a yeast-based reporter matrix to identify disease state specific pathways for targeting. For example, a reporter matrix comprising the yeast mutant $Ras^2val19$ provides a discovery vehicle for pathways specific to the human analog, the oncogene $Ras^2val12$.

Application of Novel Combinatorial Chemistries with the Two Color Global Reporter Arrays Among the most important advances in drug development have been advances in combinatorial synthesis of chemical libraries. In conventional drug screening with purified enzyme targets, combinatorial chemistries can often help create new derivatives of a lead compound that will also inhibit the target enzyme but with some different and desirable property. However, conventional methods would fail to recognize a molecule having a substantially divergent specificity. The genome reporter matrix offers a simple solution to recognizing new specificities in combinatorial libraries. Specifically, pools of new compounds are tested as mixtures across the matrix. If the pool has any new activity not present in the original lead compound, new genes are affected among the reporters. The identity of that gene provides a guide to the target of the new compound. Furthermore, the matrix offers an added bonus that compensates for a common weakness in most chemical syntheses. Specifically, most syntheses produce the desired product in greatest abundance and a collection of other related products as contaminants due to side reactions in the synthesis. Traditionally the solution to contaminants is to purify away from them. However, the genome reporter matrix exploits the presence of these contaminants. Syntheses can be adjusted to make them less specific with a greater number of side reactions and more contaminants to determine whether anything in the total synthesis affects the expression of target genes of interest. If there is a component of the mixture with the desired activity on a particular reporter, that reporter can be used to assay purification of the desired component from the mixture. In effect, the reporter matrix allows a focused survey of the effect on single genes to compensate for the impurity of the mixture being tested.

Isoprenoids are a specially attractive class for the genome reporter matrix. In nature, isoprenoids are the champion signaling molecules. Isoprenoids are derivatives of the five carbon compound isoprene, which is made as an intermediate in cholesterol biosynthesis. Isoprenoids include many of the most famous fragrances, pigments, and other biologically active compounds, such as the antifungal sesquiterpenoids, which plants use defensively against fungal infection. There are roughly 10,000 characterized isoprene derivatives and many more potential ones. Because these compounds are used in nature to signal biological processes, they are likely to include some of the best membrane permeant molecules.

Isoprenes possess another characteristic that lends itself well to drug discovery through the genome reporter matrix. Pure isoprenoid compounds can be chemically treated to create a wide mixture of different compounds quickly and easily, due to the particular arrangement of double bonds in the hydrocarbon chains. In effect, isoprenoids can be mutagenized from one form into many different forms much as a wild-type gene can be mutagenized into many different mutants. For example, vitamin D used to fortify milk is produced by ultraviolet irradiation of the isoprene derivative known as ergosterol. New biologically active isoprenoids are generated and analyzed with a genome reporter matrix as follows. First a pure isoprenoid such as limonene is tested to determine its response profile across the matrix. Next, the isoprenoid (e.g. limonene) is chemically altered to create a mixture of different compounds. This mixture is then tested across the matrix. If any new responses are observed, then the mixture has new biologically active species. In addition the identity of the reporter genes provides information regarding what the new active species does, an activity to be used to monitor its purification, etc. This strategy is also applied to other mutable chemical families in addition to isoprenoids.

Applications of the Two Color Global Reporter Arrays in Antibiotic and Antifungal Drug Discovery Fungi are important pathogens on plants and animals and make a major impact on the production of many food crops and on animal, including human, health. One major difficulty in the development of antifungal compounds has been the problem of finding pharmaceutical targets in fungi that are specific to the fungus. The genome reporter matrix offers a new tool to solve this problem. Specifically, all molecules that fail to elicit any response in the Saccharomyces reporter are collected into a set, which by definition must be either inactive biologically or have a very high specificity. A reporter library is created from the targeted pathogen such as *Cryptococcus, Candida, Aspergillus, Pneumocystis* etc. All molecules from the set that do not affect *Saccharomyces* are tested on the pathogen, and any molecule that elicits an altered response profile in the pathogen in principle identifies a target that is pathogen-specific. As an example, a pathogen may have a novel signaling enzyme, such as an inositol kinase that alters a position on the inositol ring that is not altered in other species. A compound that inhibits that enzyme would affect the signaling pathway in the pathogen, and alter a response profile, but due to the absence of that enzyme in other organisms, would have no effect. By sequencing the reporter genes affected specifically in the target fungus and comparing the sequence with others in GenBank, one can identify biochemical pathways that are unique to the target species. Useful identified products include not only agents that kill the target fungus but also the identification of specific targets in the fungus for other pharmaceutical screening assays.

The identification of compounds that kill bacteria has been successfully pursued by the pharmaceutical industry for decades. It is rather simple to spot a compound that kills bacteria in a spot test on a petri plate. Unfortunately, growth inhibition screens have provided very limited lead compound diversity. However, there is much complexity to bacterial physiology and ecology that could offer an edge to development of combination therapies for bacteria, even for compounds that do not actually kill the bacterial cell. Consider for example the bacteria that invade the urethra and persist there through the elaboration of surface attachments known as timbrae. Antibiotics in the urine stream have limited access to the bacteria because the urine stream is short-lived and infrequent. However, if one could block the synthesis of the timbrae to detach the bacteria, existing therapies would become more effective. Similarly, if the chemotaxis mechanism of bacteria were crippled, the ability of bacteria to establish an effective infection would, in some species, be compromised. A genome reporter matrix for a bacterial pathogen that contains reporters for the expression of genes involved in chemotaxis or fimbrae synthesis, as examples, identifies not only compounds that do kill the bacteria in a spot test, but also those that interfere with key steps in the biology of the pathogen. These compounds would be exceedingly difficult to discover by conventional means.

Applications of Human Cell Based Two Color Global Reporter Arrays

A genome reporter matrix based on human cells provides many important applications. For example, an interesting application is the development of antiviral compounds. When human cells are infected by a wide range of viruses, the cells respond in a complex way in which only a few of the components have been identified. For example, certain interferons are induced as is a double-stranded RNase. Both of these responses individually provides some measure of protection. A matrix that reports the induction of interferon genes and the double stranded RNase is able to detect compounds that could prophylactically protect cells before the arrival of the virus. Other protective effects may be induced in parallel. The incorporation of a panel of other reporter genes in the matrix is used to identify those compounds with the highest degree of specificity.

More Advantages of the Two Color Global Reporter Arrays

One advantage of the invention is that the strains having varying copy numbers of the target sequences (or which express the target gene product-encoding sequence at varying levels) are easy to make and collections can be customarily designed to screen for drugs that inhibit specific cellular processes and targets.

Another advantage of the invention is that it does not require overexpression of the candidate target gene product sequence, which can itself decrease growth rate or be lethal. In contrast, a subtle change in copy number (e.g., a change of plus or minus one copy) minimizes physiological effect.

Still another advantage of the invention is that the method is not dependent upon use of autonomous plasmids that are inherently unstable. Thus the problems associated with the effect of gross overexpression of a target sequence (e.g., expression of 10–50 copies) and/or the effects of bioactive compound on plasmid copy number and/or stability are avoided.

Yet another advantage is that the invention can identify multiple targets of a drug.

The method of the invention is also advantageous in that it can be used with strains that are diploid ((2n); where "n" is the target sequence), heterozygous deletion strains (2n−1), haploid (n), or contain extra copies of the target sequence (e.g., (2n+1), (n+1), etc. where extra copies are preferably chromosomally integrated), and further allows for simultaneous screening of such strains.

Still another advantage is that the invention takes advantage of available genomic information. For example, if the complete or partial sequence of a potential target gene(s) is known, then one can readily construct strains for use in the invention, even if the function of the gene is unknown.

Another advantage of the invention is that information about the function of unknown genes can be readily attained in an in vivo system. For example, identifying strains that are sensitive or resistant to a known drug may reveal genes not otherwise known to be involved in the same pathway or parallel pathways.

Another advantage of the invention is that it facilitates the discovery of new drugs (e.g., antifungal, anti-cancer, etc.) that affect the same target as known drugs, since once a heterozygous deletion strain is found to be sensitive to a known drug, this strain can then be used to find other drugs that affect the same strain.

The method of the invention is also advantageous in that it allows screening of many potential drug targets simultaneously (e.g., gene products involved in any cellular process such as DNA synthesis, assembly and function of the mitotic apparatus, sterol biosynthesis, cell wall biosynthesis, etc.), rather than testing such targets individually using conventional methods. For example, all possible targets can be tested using a collection of strains having deletions representative of the entire host cell's genome (e.g., using yeast as a host cell). Such a collection of yeast strains is presently under construction. Moreover, the invention allows for the identification of drug targets for known and new drugs alike, as well as the identification of new drugs that inhibit the same target as a known drug.

Another advantage is that, where the pathway or process inhibited by a drug is known, the method of the invention can be used to identify other drugs that affect this same pathway and that may have more specificity for a target in the pathway and/or fewer side effects than the known drug.

The method of the invention is also advantageous in that it is extremely sensitive, thus allowing detection of bioactive compounds at very low concentrations of the candidate compound. The invention thus allows discovery of drugs that would previously go undetected, and requires only a very small amount of candidate compound for screening.

Yet another advantage of the invention is that competitive growth assays are at least an order of magnitude more sensitive relative to other methods, such as methods that require measurement of colony forming units.

The invention is also advantageous in that it can facilitate identification of multiple drugs in a drug mixture or complex mixture of natural origin even if the drugs within the mixture have different targets. Furthermore, the methods allows identification of the targets.

The method of the invention is also advantageous in that it is readily adapted to high-throughput automation, is highly parallel and quantitative, and is rapid (i.e., assays can be carried out in a few hours). Moreover, because the assays do not require long term growth (e.g., more than 10–20 hrs, days, or weeks) the probability of selection for secondary mutations that might mask the effect of the true target gene is minimized.

Still another advantage of the invention is that it is relatively inexpensive to screen multiple drugs since, for example, collections of strains representing a large number of targets can be screened simultaneously in small culture volumes, and thus requires only a small amount of drug.

Another advantage of the invention is that once a target gene product(s) of a known drug is identified, the method can be used to identify other drugs that bind that same target gene product(s), thereby facilitating development of drugs that are both safe and effective, thus speeding the drug approval process.

Another advantage of the invention is that it can be readily adapted for use with a wide variety of host cells (e.g., haploid or diploid organisms; bacterial, yeast, or mammalian cells) and with a wide variety of candidate target gene product sequences.

Use of the Two Color Global Reporter Arrays

The procedures of the subject methods are illustrated herein. The initial step involves detecting reporter gene product signals from each of a plurality of different, separately isolated cells of a target organism under one or more of a variety of physical conditions, such as temperature and pH, medium, and osmolarity. The target organism may be a yeast, animal model, human, plant, pathogen, etc. Generally, the cells are arranged in a physical matrix such as a microtiter plate. Each of the cells contains a recombinant construct comprising a reporter gene operatively linked to a different endogenous transcriptional regulatory element of said target organism such that said transcriptional regulatory element regulates the expression of said reporter gene. A sufficient number of different recombinant cells are included to provide an ensemble of transcriptional regulatory elements of said organism sufficient to model the transcriptional responsiveness of said organism to a drug. In a preferred embodiment, the matrix is substantially comprehensive for the selected regulatory elements, e.g. essentially all of the gene promoters of the targeted organism are included. Other cis-acting or trans-acting transcription regulatory regions of the targeted organism can also be evaluated. In one embodiment, a genome reporter matrix is constructed from a set of LacZ fusions to a substantially comprehensive set of yeast genes. The fusions are preferably constructed in a diploid cell of the a/a mating type to allow the introduction of dominant mutations by mating, though haploid strains also find use with particularly sensitive reporters for certain functions. The fusions are conveniently arrayed onto a microtiter plate having 96 wells separating distinct fusions into wells having defined alphanumeric X–Y coordinates, where each well (defined as a unit) confines a cell or colony of cells having a construct of a reporter gene operatively joined to a different transcriptional promoter. Permanent collections of these plates are readily maintained at −80° C. and copies of this collection can be made and propagated by simple mechanics and may be automated with commercial robotics.

The methods involve detecting a reporter gene product signal for each cell of the matrix. A wide variety of reporters may be used, with preferred reporters providing conveniently detectable signals (e.g. by spectroscopy). Typically, the signal is a change in one or more electromagnetic properties, particularly optical properties at the unit. As examples, a reporter gene may encode an enzyme which catalyzes a reaction at the unit which alters light absorption properties at the unit, radiolabeled or fluorescent tag-labeled nucleotides can be incorporated into nascent transcripts which are then identified when bound to oligonucleotide probes, etc. Examples include β-galactosidase, invertase, green fluorescent protein, etc. Invertase fusions have the virtue that functional fusions can be selected from complex libraries by the ability of invertase to allow those genes whose expression increases or decreases by measuring the relative growth on medium containing sucrose with or without the compound of interest. Electronic detectors for optical, radioactive, etc. signals are commercially available, e.g. automated, multi-well colorimetric detectors, similar to automated ELISA readers. Reporter gene product signals may also be monitored as a function of other variables such as stimulus intensity or duration, time (for dynamic response analyses), etc.

In a preferred embodiment, the response profiles are determined through the calorimetric detection of a GFP and DsRed product. The optical signal generated at each well is detected and linearly transduced to generate a corresponding digital electrical output signal. The resultant electrical output signals are stored in computer memory as a genome reporter output signal matrix data structure associating each output signal with the coordinates of the corresponding microtiter plate well and the stimulus or drug. This information is indexed against the matrix to form reference response profiles that are used to determine the response of each reporter to any milieu in which a stimulus may be provided.

After establishing a basal response profile for the each matrix or the standard response profile come from mixing the two exactly same conditions matrices, each cell is contacted with a candidate drug or one of the host cell contacted with a candidate drug. The term drug is used loosely to refer to agents which can provoke a specific cellular response. Preferred drugs are pharmaceutical agents, particularly therapeutic agents. The drug induces a complex response pattern of repression, silence and induction across the matrix (i.e. a decrease in reporter activity at some units, an increase at others, and no change at still others). The response profile reflects the cell's transcriptional adjustments to maintain homeostasis in the presence of the drug. While a wide variety of candidate drugs can be evaluated, it is important to adjust the incubation conditions (e.g. concentration, time, etc.) to preclude cellular stress, and hence insure the measurements of pharmaceutically relevant response profiles. Hence, the methods monitor transcriptional changes which the cell uses to maintain cellular homeostasis. Cellular stress may be monitored by any convenient way such as membrane potential (e.g. dye exclusion), cellular morphology, expression of stress response genes, etc. In a preferred embodiment, the compound treatment is performed by transferring a copy of the entire matrix to fresh medium containing the first compound of interest.

After contacting the cells with the candidate drug, the reporter gene product signals from each of said cells is again measured to determine a stimulated response profile. The basal of background response profile is then compared with (e.g. subtracted from, or divided into) the stimulated response profile to identify the cellular response profile to the candidate drug. The cellular response can be characterized in a number of ways. For example, the basal profile can be subtracted from the stimulated profile to yield a net stimulation profile. In another embodiment, the stimulated profile is divided by the basal profile to yield an induction ratio profile. Such comparison profiles provide an estimate of the physiological specificity of the candidate drug.

In another embodiment of the invention, a matrix of hybridization probes corresponding to a predetermined population of genes of the selected organism is used to specifically detect changes in gene transcription which result from exposing the selected organism or cells thereof to a candidate drug. In this embodiment, one or more cells derived from the organism is exposed to the candidate drug in vivo or ex vivo under conditions wherein the drug effects a change in gene transcription in the cell to maintain homeostasis. Thereafter, the gene transcripts, primarily mRNA, of the cell or cells is isolated by conventional means. The isolated transcripts or cDNAs complementary thereto are then contacted with an ordered matrix of hybridization probes, each probe being specific for a different one of the transcripts, under conditions wherein each of the transcripts hybridizes with a corresponding one of the probes to form hybridization pairs. The ordered matrix of probes provides, in aggregate, complements for an ensemble of genes of the organism sufficient to model the transcriptional responsiveness of the organism to a drug. The probes are generally immobilized and arrayed onto a solid substrate such as a microtiter plate. Specific hybridization may be effected, for example, by washing the hybridized matrix with excess non-specific oligonucleotides. A hybridization signal is then detected at each hybridization pair to obtain a matrix-wide signal profile. A wide variety of hybridization signals may be used; conveniently, the cells are pre-labeled with radionucleotides such that the gene transcripts provide a radioactive signal that can be detected in the hybridization pairs. The matrix-wide signal profile of the drug-stimulated cells is then compared with a matrix-wide signal profile of negative control cells to obtain a specific drug response profile.

The invention also provides means for computer-based qualitative analysis of candidate drugs and unknown compounds. A wide variety of reference response profiles may be generated and used in such analyses. For example, the response of a matrix to loss of function of each protein or gene or RNA in the cell is evaluated by introducing a dominant allele of a gene to each reporter cell, and determining the response of the reporter as a function of the mutation. For this purpose, dominant mutations are preferred but other types of mutations can be used. Dominant mutations are created by in vitro mutagenesis of cloned genes followed by screening in diploid cells for dominant mutant alleles. In an alternative embodiment, the reporter matrix is developed in a strain deficient for the UPF gene function, wherein the majority of nonsense mutations cause a dominant phenotype, allowing dominant mutations to be constructed for any gene. UPF1 encodes a protein that causes the degradation of mRNA's that, due to mutation, contain premature termination codons. In cells lacking UPF1, function most nonsense mutations encode short truncated protein fragments. Many of these interfere with normal protein function and hence have dominant phenotypes. Thus in a upf1 mutant, many nonsense alleles behave as dominant mutations (see, e.g., Leeds et al., *Mol. Cell. Biology*, 12:2165–77 (1992)).

The resultant data identify genetic response profiles. These data are sorted by individual gene response to determine the specificity of each gene to a particular stimulus. A weighting matrix is established which weights the signals proportionally to the specificity of the corresponding reporters. The weighting matrix is revised dynamically, incorporating data from every screen. A gene regulation function is then used to construct tables of regulation identifying which cells of the matrix respond to which mutation in an indexed gene, and which mutations affect which cells of the matrix.

Response profiles for an unknown stimulus (e.g. new chemicals, unknown compounds or unknown mixtures) may be analyzed by comparing the new stimulus response profiles with response profiles to known chemical stimuli. Such comparison analyses generally take the form of an indexed report of the matches to the reference chemical response profiles, ranked according to the weighted value of each matching reporter. If there is a match (i.e. perfect score), the response profile identifies a stimulus with the same target as one of the known compounds upon which the response profile database is built. If the response profile is a subset of cells in the matrix stimulated by a known compound, the new compound is a candidate for a molecule with greater specificity than the reference compound. In particular, if the reporters responding uniquely to the reference chemical have a low weighted response value, the new compound is concluded to be of greater specificity. Alternatively, if the reporters responding uniquely to the reference compound have a high weighted response value, the new compound is concluded to be active downstream in the same pathway. If the output overlaps the response profile of a known reference compound, the overlap is sorted by a quantitative evaluation with the weighting matrix to yield common and unique reporters. The unique reporters are then sorted against the regulation tables and best matches used to deduce the candidate target. If the response profile does not either overlap or match a chemical response profile, then the database is inadequate to infer function and the response profile may be added to the reference chemical response profiles.

The response profile of a new chemical stimulus may also be compared to a known genetic response profile for target gene(s). If there is a match between the two response profiles, the target gene or its functional pathway is the presumptive target of the chemical. If the chemical response profile is a subset of a genetic response profile, the target of the drug is downstream of the mutant gene but in the same pathway. If the chemical response profile includes as a subset a genetic response profile, the target of the chemical is deduced to be in the same pathway as the target gene but upstream and/or the chemical affects additional cellular components. If not, the chemical response profile is novel and defines an orphan pathway.

While described in terms of cells comprising reporters under the transcriptional control of endogenous regulatory regions, there are a number of other means of practicing the invention. For example, each unit of a genome reporter matrix reporting on gene expression might confine a different oligonucleotide probe capable of hybridizing with a corresponding different reporter transcript. Alternatively, each unit of a matrix reporting on DNA-protein interaction might confine a cell having a first construct of a reporter gene operatively joined to a targeted transcription factor binding site and a second hybrid construct encoding a transcription activation domain fused to a different structural gene, i.e. a one-dimensional one-hybrid system matrix. Alternatively, each unit of a matrix reporting on protein-protein interactions might confine a cell having a first construct of a reporter gene operatively joined to a targeted transcription factor binding site, a second hybrid construct encoding a transcription activation domain fused to a different constitutionally expressed gene and a third construct encoding a DNA-binding domain fused to yet a different constitutionally expressed gene, i.e. a two-dimensional two-hybrid system matrix.

Illustration of Steps Involved in the Present Methods
Construction of Host Cells
Host Cells The assay of the invention can be used in connection with any of a variety of host cells, including eukaryotic, prokaryotic, diploid, or haploid organisms, with the proviso that the host cell allows for genetic manipulation to provide for adequately precise regulation of target gene expression (e.g., the copy number of a target gene can be readily manipulated between two copies and one copy and/or the host cell allows for manipulation of transcription levels of a target gene to provided for altered expression levels). Host cells can also be either single cell organisms (e.g., bacteria, e.g., *Mycobacterium* spp., e.g., *M. tuberculosis*) or multi-cellular organisms (transgenic organisms, such as insects (e.g., *Drosophila*), worms (e.g., *Caenorhabditis* spp, e.g., *C. elegans*) and higher animals (e.g., transgenic mammals such as mice, rats, rabbits, hamsters, etc.). Preferably the host cell is a naturally diploid cell, preferably yeast cells (e.g., *Saccharomyces* spp. (e.g., *S. cerevisiae*), *Candida* spp. (e.g., *C. albicans*)) or mammalian cells. The host cell can also be a cell infected with a virus or phage that contains a target sequence in the viral or phage genome.

Yeast are currently a particularly preferred host cell for the method of the invention. Specifically, yeast naturally provides a powerful, easily genetically manipulatable model system which naturally contain target sequences of potential interest. For example, biochemical pathways exclusive to fingi can be enfeebled via gene disruption and potential drugs identified based on increased sensitivity to specific drugs compared with wildtype (Kirsch, *Curr Opin Biotechnol.*, 4(5):543–552 (1993)). Moreover, because of the extensive homology shared between yeast and human proteins (Foury, *Gene*, 195:1–10 (1997)), yeast can also be exploited to assay human drug targets by expressing a potential human drug target in the yeast host in lieu of the yeast homolog. Furthermore, identification of a target in yeast that shares homology with a human gene product can also provide information about the interaction the drug with the human homolog. Thus, the yeast provide a genetically manipulatable host cell, a genome encoding potentially interesting target sequences, and a system for expression of recombinant sequences from other organisms, especially human sequences. In general any method that results in target gene expression levels that provide for detectably different phenotypes (e.g., a detectable difference in growth rate) in the method of the invention can be used to generate strains for use in the claimed invention; Such methods include, but are not limited to, methods that alter the number of copies of the target gene (e.g., by decreasing target gene copy number (e.g., by deletion or otherwise rendering a target gene copy nonfunctional) or by increasing target gene copy number (e.g., by introducing an additional copy(ies) of the target gene), as well as methods that otherwise alter target gene expression levels in the host cell (e.g., by alteration of transcription levels (e.g., through use of a mutated native promoter or a heterologous promoter, including constitutive and inducible promoters), or by alteration of translation of target gene transcripts). Preferably, target gene expression is altered by altering copy number of the target gene.

Target Genes

The strains used in the invention can be altered in expression (e.g., by altering copy number or otherwise affecting transcription levels) of any gene of interest. It is not necessary that the function of the product encoded by the target gene be known; rather, the method of the invention can be used to determine whether the encoded unknown gene product plays a role in survival of the strain under a given set of conditions (e.g., presence of drug, increased temperature, nutrient-deficient medium, etc.). Thus, the target genes can encode any of a variety of gene products, including, but not limited to, genes encoding a protein having an enzymatic activity, structural genes (i.e., DNA sequences which encode a protein or peptide product), regulatory genes (i.e., DNA sequences which act as regulatory regions, such as promoters, enhancers, terminators, translational regulatory regions, etc., to affect the level or pattern of gene expression), and DNA sequences that encode a bioactive RNA, such as an antisense RNA (i.e., to provide for inhibition of expression of a host DNA sequence), or structural RNAs (i.e., RNAs with enzymatic activities or binding activities (ribozymes).

The method of the invention is not limited to examination of the role of "essential" genes, i.e., genes that are conventionally thought to be necessary for cell growth under a given condition or set of conditions. Rather, the invention recognizes that the concept of "essential" genes has hindered the discovery of genes with duplicative function or genes in duplicate pathways that can facilitate resistance to drugs that are targeted against "essential" genes. The exquisite sensitivity of the claimed method can be used to unmask such "nonessential" genes that encode potential drug targets of interest, thus facilitating the design of drugs that can be used alone or in combination with conventional drugs to minimize selection of resistant strains, reduce the amount of drug or the time of administration necessary to combat disease, and thus provide a means to avoid side effects associated with administration of high dosages or lengthy drug courses (e.g., toxicity to the subject and other side effects).

Constructing Host Cells Containing Two Different Reporters With Same or Different Copy Numbers of Candidate Target Gene Product-encoding Sequences In one embodiment, the method of the invention employs strains having same or precise, varying copy numbers of the target sequence of interest. In any given strain, the copy number of the target sequence (i.e., the number of functional copies of the target sequence) is preferably either same or exactly two (i.e., diploid wildtype), exactly one (i.e., heterozygous deletion strain), or exactly three. As used herein "target sequence copy number" refers to the number of functional target sequences contained and expressed in a host cell. By "functional target sequence" is meant a nucleotide sequence that is expressed in the host cell to provide a functional gene product, i.e., a wildtype gene product that can serve its ordinary structural, enzymatic, or other function in the host cell.

The method of the invention can be used to analyze the effects of varying copy number of a single target sequence or to analyze simultaneously the effects of gene dosage of hundreds to thousands of different target sequences. For example, the cell population can comprise only one heterozygous deletion strain (and thus involve analysis of only one target sequence) or can comprise 10, 100, 500, 1,200, 6,200, or more heterozygous deletion strains (and thus the corresponding number of target sequences). The heterozygote strains used in the method can contain deletions in genes which collectively represent a set of gene of interest, such as the host cell's complete or partial genome. For example, where the host cell is yeast, the heterozygote strain collection can contain deletions in each of the approximately 6,000 genes of the yeast genome. Alternatively, the collection of heterozygotes can be tailored to screen a desired set of genes. For example, the heterozygote strain collection can contain deletions only in sequences encoding proteins for which a drug that specifically targets that gene product is desired (e.g., to find anticancer drugs that have the same target as benomyl using a tub1.DELTA./TUB1 or a tub2.DELTA./TUB2 strain).

Heterozygote Construction

Heterozygous deletion strains for use in the invention are constructed by site-specific deletion of a genomic sequence according to methods well known in the art. The site-specific deletion can be accomplished by using tagged transposons and retrospectively identifying strains containing the tagged transposons inserted into a desired gene. Alternatively, site-specific deletions can be generated using homologous recombination (e.g., Rothstein et al. 1991, supra). Where the host cell is a yeast cell, the heterozygotes are preferably constructed according to the methods of Rothstein, *Meth. Enzymol.*, 194:281–301 (1991), combined with the construction of strains containing molecular tags as per the method of Shoemaker et al., *Nature Genetics*, 14:450 (1996), which involves incorporation of a molecular tag during the site-specific deletion process. The wildtype diploid host cell having a tag inserted in a non-functional gene can serve as the reference strain.

Of particular interest in the invention is the identification of strains that are haploinsufficient in the presence of drug, i.e., strains that display a growth rate phenotype in the presence of drug as a result of the presence of only one copy of the target gene. Identification of haploinsufficient strains indicates that even subtle change in gene dosage affect the fitness of the cell. Identification of haploinsufficient strains can have direct implications for drug therapy and the recommended therapeutic dosages and course. For example, identification of a drug that targets a gene product that is associated with haploinsufficiency in a heterozygous deletion strain suggests that the drug need only be administered in an amount that decreases the function of the gene product by about one-half; administration of an amount of drug sufficient to bind or inhibit function of all of the gene product may be unnecessary and even toxic, and may only serve to increase selective pressure for mutations in the target gene product.

In one embodiment, the method of the invention employs two complete genomic sets of genetically tailored yeast strains potentially sensitized or resistant to every possible drug target coded by the yeast genome. The first set is comprised of 6,000 heterozygote mutants (2n−1), with each strain carrying a deletion of a single genetic locus. In the second set, the gene dosage of every gene is systematically increased from one to two copies. This is accomplished by integrating a second copy of the target gene into the genome (2n+1). Production of such a collection of tagged heterozygous deletion strains is currently being carried out by a fifteen-lab international consortium. This collection of barcoded deletions will be available at http://sequence-www.stanford.edu/group/yeast.sub.—deletion sub.—project deletions3.html.

The results of the method of the invention can be further confirmed, and the identified target further characterized, by producing host cells containing more than two copies of a target sequence. For example, strains containing three or more copies of the target sequence can be used to confirm results from analysis of strains containing one or two copies of the identified target sequence. Host cells containing more than two functional copies of a target sequence can be generated according to methods well known in the art. Preferably, such strains are generated by introducing the target sequence as a single copy in the chromosome (to produce a strain having a total of 3 copies of the target sequence) or on a multicopy plasmid such as CEN or a 2.mu. circle (also known as Scp1), which provide for 5–10 copies and 60–80 copies of a target sequence, respectively (see, e.g., Rine et al., *Proc. Natl. Acad. Sci. USA*, 80:6750–6754 (1983)).

Construction of Host Cells Having Altered Levels of Expression of a Target Sequence by Altering Promoter Activity The method of the invention encompasses identification of drug targets by altering expression of the sequence encoding the drug target. Alteration of target sequence copy number (e.g., from two copies to one copy) is only one means by which manipulation of target sequence expression can be achieved to facilitate identification of drugs targets according to the method of the invention. Alteration of target gene expression can also be accomplished by specifically altering the native promoter of the target gene. Alteration of target gene expression can also be achieved by construction of strains carrying a conditional mutation in a target gene, where the strain contains, for example, a temperature sensitive mutation in one copy of the target gene, which mutation renders the gene nonfunctional when grown at certain temperature. Alternatively, target gene expression can be altered by expression of antisense RNA to decrease expression of the target sequence. Thus, strains referred to herein as strains having "altered expression levels of a target gene" are thus meant to encompass strains having varying target gene copy number as well as strains containing other genetic alterations that provide for differences in transcription of a specific target sequence, e.g., by introduction of a heterologous promoter that facilitates transcription of the target gene in lieu of the native target gene promoter.

Alteration of transcription levels of the target gene can be accomplished by site-specific mutation of the native target gene promoter, or by replacement of the native promoter with a heterologous promoter. Methods for site-specific promoter alteration to affect alteration of transcription levels directed by the promoter (e.g., increase or decrease in transcription relative to the native promoter), as well as methods for introduction of heterologous promoters to drive transcription of a genomic sequence are well known in the art. Exemplary promoters include, but are not limited to, very weak constitutive promoters (e.g., yeast promoter KEX2), regulated promoters (e.g., the yeast promoters CYC1, PGK, and the yeast mating type-specific promoter MFα1), strong constitutive promoters (e.g., the yeast promoters TEF1, TDH), and inducible or repressible promoters (e.g., the yeast promoters GAL1, GAL7, GAL10, ADH1, ADH2, MT, PHO5), as well as promoters that provide for temperature-sensitive expression of the target gene. Methods for constructing strains having such heterologous promoters, and methods for inducing and/or maintaining a desired transcription level, and methods for qualitatively and/or quantitatively measuring transcriptional levels are well known in the art.

Exemplary promoters and such methods for their use are described in Nacken et al., *Gene*, 175:253 (1996) (relative transcription levels of KEX2, CYC1, PGK, MF.alpha.1, TEF1, and TDH); Mylin et al., *Meth. Enzymol*, 185:297 (1990) (GAL1, GAL7, and GAL10; also describing use of the GAL expression system to obtain up to 60-fold increase in expression by using a strain containing both the chromosomal wildtype GAL4 gene and an expression cassette consisting of the GAL4 structural gene fused to the GAL10 promoter); Schneider et al. 1991 Meth. Enzymol. 194:373 (describing the GAL promoter system to provide regulated expression (e.g., using GAL1, which can provide 1000-fold induction in the presence of galactose and repression of expression in the presence of glucose), the ADHI promoter (which can provide 2-fold to 10-fold repression of expression in the presence of a nonfermentable carbon source), and the PGK promoter (which can provide for 20-fold to 30-fold repression of expression in the presence of a nonfermentable carbon source); Price et al. 1990 Meth. Enzymol. 185:308 (describing use of the ADH2 promoter to provide regulation of expression by glucose repression); Etcheverry 1990 Meth. Enzymol. 185:319 (describing use of the inducible MT promoter); Schena et al. 1991 Meth. Enzymol. 194:389 (describing use of the inducible strong promoter PHO5, the high-level constitutive yeast glyceraldehyde-3phosphate dehydrogenase promoters (see also Schneider et al, supra), and glucocorticoid-inducible yeast expression vector p2UG in conjunction with the glucocorticoid receptor-encoding vector pG-N795). Additional promoters and expression systems are described in Emr 1990 Meth. Enzymol. 185:231; Rose et al. 1990 Meth. Enzymol. 185:234; Steams et al. 1990 Meth. Enzymol. 185:280; Kingsmen et al. 1990 Meth. Enzymol. 185:329; Rosenberg et al. 1990 Meth. Enzymol. 185:341; and Sledziewski 1990 Meth. Enzymol 185:351. Also see generally Goeddel (ed.) 1990 Expression in Yeast. Methods in Enzymology 185 Section IV., Academic Press, San Diego, Calif.

Transcription levels can also be increased by introduction of additional copies of the target gene. This can be accomplished by, for example, introduction of an autonomous plasmid, which can be (and preferably is) chromosomally integrated into the genome of the host cell. Such autonomous plasmids are well known in the art and include, but are not limited to, 2-micron circle-based vectors (see, e.g., Rose et al., supra; Rose et al., supra), centromere-based (YCp) vectors, and ARS-based vectors (Rose et al., supra). For additional vectors useful in the invention, see Schena et al., supra (describing the pG-1, pG-2, pG-2, and p2UG/pG-N795 expression vector systems). The various promoters mentioned above can be used in conjunction with such plasmids to further increase expression levels of the target gene (see, e.g., Nacken et al., describing that a 3-log difference in expression levels of a gene can be obtained by varying promoter strength only, while introducing a single to high copy number plasmid can add an additional 100-fold increase in expression).

Preferably, the method of the invention uses strains that differ subtly in expression of the target gene, e.g., by at least about half-fold, by at least about 2-fold (e.g., a two copy strain compared to a one copy strain), by at least about 3-fold, by at least about 4-fold, and up to about 5-fold to about 10-fold or more. In general, expression levels of the target gene can be altered from about 0.5-fold to about 1,000-fold, and can be from about 0.1-fold to 10,000-fold. Preferably the expression levels differ by less than about 10-fold and may be less than about 5-fold. The method of the invention can also be used in conjunction with strains that differ in expression of the target gene by greater degrees (e.g., by about 100-fold to about 1,000-fold) providing that the target gene expression allows for detection in growth rate differences between the strain grown in the presence and absence of drug relative to the growth rate of a strain having a differing level of expression (e.g., relative to wildtype) in the presence and absence of drug.

The method of the invention can also be used in conjunction with host cells containing multiple mutations. For example, the strain can contain a "double knock-out," i.e., the strain is deleted for two different genes, and thus is a "double heterozygote deletion strain." Since some mutations may only demonstrate an effect in the context of a second mutation, the use of strains containing multiple mutations may reveal additional targets.

Molecular Bar-coding

Preferably, the strains used in the method of the invention are designed to contain a molecular tag. A "molecular tag," also known as a molecular bar code, can be a nucleotide sequence, usually of about 20 nucleotides in length, which is unique to the altered gene with which it is associated. The molecular tags are preferably designed so that all tags in a host cell culture of the invention can be amplified with a single set of common primers (see, e.g., Shoemaker et al., 1996 Nature Genetics 14:450) and quantitatively identified by hybridization. This embodiment thus facilitates analysis of a large number of strains, each of which contains a deletion or other target gene alteration associated with a unique tag, in a highly parallel fashion. Moreover, use of molecular tags allows pooling of strains having differing target gene expression levels (e.g., pooling of heterozygote and diploid strains). Methods for preparation of molecular tags (Shoemaker et al., 1996 Nature Genetics 14:450) and production of strains (Rothstein (1991) Meth. Enzymol. 194:281) containing such tags are well known in the art.

An exemplary method of generating tagged heterozygous deletion strains is illustrated below. Briefly, a selectable marker, such as a kanamycin resistance gene, is amplified using a pair of long primers (e.g., 86mer and 68mer). The first primer contains a targeting sequence that has homology to the 5' end of the target genomic sequence to be deleted, while the second primer contains a targeting sequence having homology to the 3' end of the target sequence. One of either the first or second primers is also designed to contain a molecular tag (e.g., a 20 bp unique nucleotide sequence) as well as common tag priming sites flanking the molecular tag sequence. The common tag priming sites, which are generally about 18 bp in length, are common to all molecular tags used in any one set of strains to be used in the method of the invention. Thus the common tag priming sites of all heterozygote and diploid strains in a set of strains can be amplified using a single set of primer sequences that are homologous to the common tag priming sites.

The heterozygous deletion strains can be constructed by introducing the amplified selectable marker into the host cell's genome in a site-specific manner, thus rendering one of the target sequences non-functional. Where the host cell is a yeast strain, the amplified selectable marker containing the molecular tag can be transformed into a haploid yeast strain, the marker integrated into the target sequence by homologous recombination, and the resulting haploid deletion strain mated to produce a diploid strain that is heterozygous for the target sequence. More simply, the amplified selectable marker can be transformed into a diploid yeast strain to directly produce a heterozygous deletion strain (e.g., for essential genes). In contrast to the method for generation of haploid deletion strains described in Shoemaker et al., supra, it is of great importance to the present invention that the final heterozygous deletion strain contain one non-functional copy of the target sequence (due to insertion of the selectable marker) and one functional copy of the target sequence, but is otherwise diploid for all other non-target sequences.

In an especially preferred embodiment, the strains used in the invention contain two tags for each gene to be analyzed. An exemplary scheme for generating such stains having two tags is described below. Construction of strains containing two tags is similar to that described above for construction of strains containing a single tag, with the exception that both the primer containing homology to the 5' sequence of the target gene and the primer containing homology to the 3' region of the target gene contain tag priming sties and tag sequences. Use of two tags increases the sensitivity and multiplies the probability of identifying a strain correctly. Moreover, use of two tags decreases the incidence of errors or other problems in strain identification due to errors associated with tag synthesis or mutation of tag sequences during growth. Given the description of these two tagging strategies, it will be apparent to one of ordinary skill in the art that these strategies can be modified to construct strains having any number of tags, as well as construction of strains having tags that render one or more target sequences which a tag is associated non-functional.

Tagged diploid strains can be constructed in a manner similar to the construction of the haploid strains, except that the target sequence is a non-functional sequence, i.e., a sequence that does not substantially affect the diploid strain's growth rate or fitness under any growth conditions that may be used in the method of the invention. Examples of such non-functional genes include genes that are non-functional and duplicated, that have been altered to render the gene non-functional, but yet does not affect the strain's growth rate, and/or pseudogenes. For example, where the host cell is a yeast strain, the nonfunctional sequence that is tagged in the diploid strain is a non-functional HO gene, which when functional facilitates switching of mating types. Non-functional sequences suitable for tag insertion can be identified by making strains having tags in different is 5 candidate non-functional genes and testing such strains to determine the insertion of the tag has a detectable affect on growth rate of the strain. Tagged control strains, such as the tagged diploid strain described above, can contain two or more tags in the same or different non-functional gene(s).

Tagged strains having altered expression of a target sequence due to the presence of a heterologous promoter (e.g., an inducible promoter or a promoter having a promoter strength different from the native target gene promoter) can be constructed in a manner similar to that described above (e.g., by introduction of the molecular tag sequence concomitant with replacement of the native promoter). It is not necessary that the molecular tag be at or near the site of the genomic alteration (e.g., the site of the site-specific deletion or at the site of promoter alteration). Rather, it is only necessary that the molecular tag be present within the same cell, preferably on a stable episomal element or in the genome, in a manner that does not affect any functional genes in the strain (i.e., does not affect strain growth or fitness) and uniquely identifies the strain (e.g., the molecular tag identifies the strain as the strain that contains the particular site-specific deletion, or the particular promoter alteration).

Test Growth Conditions for Comparison Growth Rate/Fitness

The strains having differing levels of target gene expression (e.g., a diploid (two copy) and a heterozygous deletion (one copy) strain) can be grown under any of a variety of conditions to identify gene products that are important for growth under the given condition. For example, the method of the invention can be used to identify gene products important in growth of host cells under temperature extremes (e.g., high or low temperature), varying ionic conditions (e.g., high concentrations of salt), or pH extremes (e.g., acid or basic culture conditions). Of particular interest is the identification of gene products important in the growth of strains in the presence of a bioactive compound (i.e., drug) or in the presence of a candidate bioactive compound (i.e., candidate drug). Preferably strains are also grown in the absence of drug as a control. Strains can be grown in either liquid or on solid medium, preferably liquid medium. Where the strains are grown in liquid culture, the strains can be grown in small volumes (e.g., a volume of about 100 ul, about 200 ul, about 300 ul, about 500 ul, about 1 ml, or about 5 ml).

Differences in growth rate can be assessed by any of a variety of means well known in the art. For example, growth rate can be determined by measuring optical density (OD) as a function of time according to methods well known in the art. Preferably differences growth rate are detected using the molecular bar coding and microarray strategies described herein. In general, as used herein, "growth rate" means the generation time or doubling time of the host cell. Thus an increase in growth rate is associated with an decrease in generation time or doubling time, while a decrease in growth rate is associated with an increase in generation time or doubling time. Growth rate differences as small as about 5% and even less than or about 1% can be detected using the method of the invention. In general, the strains being analyzed are grown competitively in a single pool, where the starting pool is composed of strains at equal abundance. Where molecular tags and microarrays are used to assess growth rate, growth rate differences in the strains are detected by detection of a depletion of the strain's tag hybridization signal over time.

Bioactive Compounds for Analysis

Bioactive compounds suitable for analysis are normally initially identified as modifiers of a process, whereby their modifying effect can provide the basis for an in vivo selection. For example, in the simplest case, the modifying effect can be cell death, or severe growth rate inhibition. A "candidate bioactive compound" or "candidate drug" can be a natural or synthetic compound that may have the characteristics of a drug in the alteration of a biological process either by interaction with the same target or a different target.

The method of the invention can be used to identify the gene product targets of any bioactive compound (or candidate bioactive compound) that has a modifying effect that can provide the basis for an in vivo selection. Bioactive compounds (or candidate bioactive compounds) suitable for analysis using the claimed method include, but are not limited to, antibiotics (e.g., antibacterial, bacteriostatic, and antifungal agents), chemotherapeutic agents, agents that affect (inhibit or enhance) a biosynthetic pathway, and the like.

According to the method of the invention, the modifying effect of the bioactive compound examined is growth inhibition of a host cell, which can be manifested as, for example, a lag in doubling time of a culture, and can be as severe cell death after culturing the host cell in the presence of the agent.

Growth Conditions

The test growth condition can be any condition that allows for detection of a difference in growth of strains expressing the target gene sequence at differing levels (e.g., a difference in growth of diploid and heterozygous deletion strains). Test growth conditions can include, but are not limited to, growth in minimal media, growth under a given temperature or temperature range, or growth in the presence of a bioactive compound or candidate bioactive compound, e.g., an inhibitory compound. Preferably, a control cell culture is grown in parallel under control growth conditions that are amenable to normal host cell growth (e.g., in the absence of drug or in complete medium). Where the growth condition involves the presence of an inhibitory drug (or a candidate drug), the drug is present in the culture at a concentration sufficient to allow detection of a difference in growth rates between the strains being tested (e.g., between a two copy (diploid) strain and a one copy (e.g. heterozygote deletion) strain). Where the host cells are yeast, the growth conditions are normally in YPD medium at 30° C. either with or without drug.

The strains are grown under the growth conditions (e.g., in the presence and absence of drug) for a period sufficient to detect any difference in growth rates of the strains. In general, such growth rate differences can be detected after about 2 hours growth or less, usually at about 2 to 4 hours growth, generally within about 4 to 6 hours growth, normally within about 6 to 8 hours growth, and normally do not require more than about 10 hrs to about 12 hours growth for detection. In general, growth rate differences can be detected in less than 12 hours of growth. Stated differently, growth rate differences can be detected in about 2 generations to 4 generations, usually in about 3 generations to about 4 generations, more usually in about 4 generations to about 5 generations, and can be observed in about 8 to 10 generations, usually within or less than 10 generations. Thus, because the assays do not require long term growth (e.g., the assay does not require long-term growth of more than 24 hours or even a week as in conventional assays), the present invention minimizes the likelihood of selection of strains containing secondary mutations.

The method of the invention can be made even more sensitive to slight differences in expression of a target gene by globally decreasing transcription of all genes, e.g., by use of actinomycin in the cultures. The effects of target gene expression upon growth rate can also be examined under differing growth conditions, e.g., in media of differing nutrient composition (e.g., to simulate differing in vivo environments), as well as differing temperatures (e.g., to simulate the body temperature of the subject that may receive therapy using the identified drug or drug being tested).

Identification of Target Gene Product-Encoding Sequences and/or Bioactive Compounds After growth under a test condition as described above, the effect upon strain growth rate is analyzed. Where the strains are designed to contain a molecular tag, the relative abundance of each of the tagged strains can be determined by amplifying the tags using conventional PCR methods and the appropriate common primers. The amplified tags are then analyzed to compare, either quantitatively or qualitatively, the relative amounts of, for example, each heterozygote tag and diploid tag in a sample. The relative amounts of the tags are correlated to the relative abundance of the strains in the sample.

Analysis of the amplified tags can be accomplished according to any of a variety of methods well known in the art that allows for differentiation of the tag sequences. For example, where the tag sequences are of sufficiently different lengths, the tag composition in a sample of amplified tags can be analyzed using Southern hybridization techniques, or by hybridization to filters having bound sequences complementary to the tags.

Molecular Tag Analysis Using an Oligonucleotide Array

Preferably, the composition of the amplified tag sequences is analyzed by hybridizing the amplified tags to a high-density oligonucleotide array containing all tag sequences in the population (see Shoemaker et al. (1996) Nature Genet. 14:450). Methods for making oligonucleotide arrays useful in the present invention are well known in the art (see, e.g., Fodor et al., 1991 Science 251:767–73; Pease et al. 1994 Proc. Natl. Acad. Sci. USA 91:5022–26; Chee et al. 1996 Science 274:610–4; Lipshutz et al. 1995 BioTechniques 19:442–7). The arrays can contain thousands of oligonucleotides (e.g., 20mer oligonucleotides) representing the set of molecular tags in the total starting cell population. The tag for each of the different strains in the culture hybridizes to a known location on the array, thus facilitating identification of the specific strains that, with increasing culture time or drug concentration, exhibited decreasing (or increasing) hybridization signals on the arrays. In this manner, all molecular tags present in the population can be simultaneously identified without the need for cloning or sequencing. Moreover, it is possible to analyze tags from several time points taken during the course of the growth study. The amplified tags from each time point can be used to calculate the growth rate of their corresponding strains in the pool.

Amplified sequences can be labeled by, for example, incorporation of a labeled nucleotide (e.g., a fluorescent nucleotide such as Cy3-dUTP or Cy5-dUTP, or a radioactive nucleotide). Labeling can be accomplished by adding detectably labeled nucleotides to a standard PCR reaction containing the appropriate common primers. Unincorporated labeled nucleotides are removed (e.g., by size exclusion chromatography) prior to analysis. Alternatively, the amplified tags can be labeled by virtue of a label bound to a common primer used during amplification.

Hybridization of the labeled sequences to the microarray is accomplished according to methods well known in the art. Hybridization is carried out under hybridization conditions that allow for specific hybridization of the amplified tags to their respective complementary sequence located on the array without significant non-specific cross-hybridization. Where the molecular tags are about 20 nucleotides in length, hybridization is preferably carried out in a hybridization mixture of 6× SSPE-T (0.9 M NaCl, 60 mM $NaH_2PO_4$, 6 mM EDTA, and 0.005% Triton X-100) for 20 min at 37° C., followed by 10 washes in 1×SSPE-T at 22° C. Following hybridization, the microarrays can be scanned to detect hybridization of the amplified molecular tags using a custom built scanning laser microscope as described in Shalon et al., (1996) Genome Res. 6:639.

The relative intensity of the hybridization signals for each tag is determined according to methods well known in the art. The relative hybridization signals can be compared qualitatively to, for example, identify heterozygous strains that are depleted from the sample relative to the diploid strain. Where multiple samples of the same set of heterozygous deletion strains is compared, the relative hybridization signals of the deletion and diploid strains can be compared across samples to identify heterozygote strains that become under- or overrepresented with, for example, increasing culture time or increasing drug concentration. Where quantitative results are desired, the relative hybridization signal intensities for each strain can be compared over time with the hybridization signal intensities of a control strain (e.g., wildtype).

Strains that become underrepresented with increasing culture time (or with increasing drug concentration) relative to a strain expressing the target gene at a higher expression level (e.g. a heterozygote strain that becomes underrepresented relative to a diploid strain) are strains that express a lower level of a target gene that confers a selective advantage under the test growth conditions. For example, where the growth conditions include the presence of a growth-inhibiting drug, the depleted heterozygote contains a deletion in a target sequence encoding a gene product that confers resistance to the drug.

The use of an oligonucleotide array allows for quantitative, sensitive, and simultaneous screening of large numbers of heterozygote strains. For example, tags amplified from a pool containing 6,200 different heterozygotes, at equal abundance, should generate 6,200 hybridization signals of equal intensity on the array. However, depletion of a heterozygous deletion strain (e.g., due to sensitivity to an inhibitory compound) can be detected by a decreased hybridization signal relative to signals of the same strains at earlier time points, relative to other heterozygous deletion strains, and relative to the reference strain (e.g., a tagged wildtype strain). Inclusion of at least one molecular tag to identify each individual heterozygous deletion strain and diploid strain within a collection of strains in a culture facilitates screening of drugs in parallel and allows the method of the invention to be automated.

The combination of growth of pooled strains under test conditions and DNA microarrays according to the present invention provides a system of target identification that is potentially genome-wide as well as parallel, highly efficient, and sensitive. By utilizing DNA microarrays and PCR amplification of molecular tags, all strains in the test population can be detected and identified simultaneously, even when individual strains differ greatly in their relative abundance. Moreover, microarrays allow very large numbers of different sequences (e.g., up to about 400,000 different oligonucleotides on a single chip of about 1 sq. in.), thus enabling application of complex probes to whole genome representations for rapid analysis.

Experimental procedures for carrying certain steps of the present methods, such as construction of heterozygous deletion strains, growth of such heterozygous deletion strains, testing such heterozygous deletion strains for unknown drug targets and/or sensitivity, screening of potential targets of unknown function and screening multiple candidate drugs are known in the art and/or are disclosed in the following references, e.g., U.S. Patent Nos. 5,569,588 and 6,046,002, the disclosures are incorporated by reference in their entirety.

References

U.S. Pat. No. 4,981,784,
U.S. Pat. No. 5,569,588,
U.S. Pat. No. 5,811,231,
U.S. Pat. No. 5,807,522,
U.S. Pat. No. 5,777,079,
U.S. Pat. No. 5,965,352,
U.S. Pat. No. 5,968,738,
U.S. Pat. No. 5,989,835,
U.S. Pat. No. 6,046,002,
WO 94/17208,
DeRisi et al., "Use of a cDNA microarray to analyze gene expression patterns in human cancer" Nat Genet (Dec. 1996) 14(4):457–460,
DeRisi et al., "Exploring the metabolic and genetic control of gene expression on a genomic scale" Science (Oct. 1997) 278(5338):680–686, and
Lashkari et al., "Yeast microarrays for genome wide parallel genetic and gene expression analysis" Proc Natl Acad Sci USA (Nov. 1997) 94(24):13057–13062.

G. EXAMPLE

Strain Construction and Drug Treatment

The Strain of *Saccharomyces cerevisiae* used in this study, YHL003L (MATa his3D1 leu2DO met15DO ura3DO lag1DO::kanMX4), was derived from S288c. The cells were grown in YPD (rich medium) or minimal media supplemented with histidine, uracil, lysine, methionine, and adenine, in the presence of kan at 30° C.

Here we describe an approach for the construction of GFP and DsRed strains. Such a construction uses the one step PCR amplification methods (Baudin, A., Ozier-Kalogeropoulos, O., Denouel, A., Lacroute, F. & Cullin, C. A simple and efficient method for direct gene deletion in *Saccharomyces cerevisiae*. Nucleic Acids Research. 21, 3329–3330 (1993)). The coding region of the GFP was amplified by PCR using the oligonucleotides 5p-kan-GFP (5'-CGTACGCTGCAGGTCGACCGTAAAGGAGAA GAACTT-3') (SEQ ID NO:1) and 3p-kan-GFP (5'-ATCGATGAATTCGAGCTCGTTTGTATAGTTCAT CCAT-3') (SEQ ID NO:2). The coding region of the DsRed was amplified by PCR using the oligonucleotides 5p-kan-DsRed(5'-CGTACGCTGCAGGTCGACAGGTCTTCCAA GAATGTT-3')

(SEQ ID NO:3) and 3pkan-DsRed (5'-ATCGATGAATTCGAGCTCGAAGGAACAGATGGTGGCG-3') (SEQ ID NO:4). PCR conditions used in the experiment are as follows:

3 min, 94° C. (initial denaturation);
→15 sec, 94° C.;
35 cycles:→15 sec, 57° C.;
→60 sec, 72° C.; and
3 min, 72° C. (final elongation).

Following the PCR amplification, the crude mix was directly used to transform yeast by standard procedures (Gietz, D., St Jean, A., Woods, R. A. and Schiestle, R. H., (1992) Nucleic Acids Res. 20, 1425). All the GFP or DsRed transformants tested by replicate to minimum media contain Kan and analyzed by Southern blot. We obtained more than 10 kanS transformants and there are about 6 clones that are positive for GFP or DsRed when tested by Southern blot.

The drug treatments were performed by adding the drugs (such as canavanine or cycloheximide) directly to the liquefied medium during preparation. All drugs were purchased commercially. Stock solutions of drugs were prepared in 100% solvent (e.g., DMSO, methanol, or water). The final concentration of each drug is about a few ug/ml, e.g., 0.1–10 ug/ml.

Determination of Reporter Gene Expression Levels

Prior to each experiment, fresh dilutions of the reporter-containing strains were inoculated and grown overnight at 30° C. The fresh cultures were then arrayed onto solid medium. The drugs were added to the solid medium during preparation. Once arrayed, each plate was grow at 30° C., usually, for 21 hours. The level of the fluorescence expressed from each reporter gene fusion was determined using a Molecular Dynamics Fluorimager.

Generally, the drug treatments were performed at several concentrations (0.1 ug/ml, 1 ug/ml, and 10 ug/ml), with the analysis based upon the concentration producing the most informative expression profile. The cells containing the GFP construct had green fluorescent light and the cells containing the DsRed construct had red fluorescent light. When the two types of cells were mixed, a color between green and red was observed. In one experiment, the cells containing the GFP construct were treated with the drugs. Such treated cells were then mixed with untreated cells containing the DsRed construct and gave a color that was between green and red, but was observably different from the mixture of untreated cells containing the GFP and the DsRed constructs. In another experiment, the cells containing the DsRed construct were treated with the drugs. Such treated cells were then mixed with untreated cells containing the GFP construct and gave a color that was between green and red, but again was observably different from the mixture of untreated cells containing the GFP and the DsRed constructs.

The above descriptions and examples are included for illustrative purposes only and is not intended to limit the scope of the invention. Since modifications will be apparent to those of skill in this art, it is intended that this invention be limited only by the scope of the appended claims.

What is claim is:

1. A method of screening for a modulator of production of a target gene product, which method comprises:
   a) constructing a first host cell containing a first reporter gene encoding a first flourescent protein operatively linked to a nucleotide sequence comprising at least the promoter portion of a target gene and constructing a second host cell containing a second reporter gene encoding second flourescent protein operatively linked to said nucleotide sequence to which said first reporter gene is linked, wherein expression of said first reporter gene results in a first flourescently detectable signal, expression of said second reporter gene results in a second flourescently detectable signal, said first and second flourescently detectable signals are distinct from each other but are integratable, and wherein said first and second host cells grown separately and then mixed to produce a third flourescently detectable signal distinct from said first and second flourescently detectable signals and detention of said third flourescent signal does not depend on the continued growth or viability of said first and second host cells;
   b) detecting said third flourescently detectable signal from a mixture of said first and second host cells wherein neither type of said host cells is subjected to any desired treatment;
   c) detecting said third flourescently detectable signal from a mixture of said first and second host cells wherein one and only one type of said host cells is subjected to a desired treatment prior to said mixing of said host cells; and
   d) comparing said third flourescently detectable signals detected in steps b) and c), whereby said third flourescently detectable signal detected in step b) differs from that detected in step c) identifies said treatment as a modulator of production of said target gene product, wherein the method is performed in vitro.

2. The method of claim 1, wherein the first and second host cells are identical strain or cells.

3. The method of claim 1, wherein the first and second host cells are identical strain or cells.

4. The method of claim 1, wherein the first and second host cells belong to two different species of the same or different genus.

5. The method of claim 1, wherein the host cells are selected from the group consisting of animal, plant, fungus, bacterium, viral infected and recombinant cells.

6. The method of claim 5, wherein the fungus cells are yeast cells.

7. The method of claim 6, wherein the yeast cells are *S. cerevisiae* cells.

8. The method of claim 5, wherein the animal cells are selected from the group consisting of fly, worm, insect, vertebrate and mammalian cells.

9. The method of claim 8, wherein the mammalian cells are human cells.

10. The method of claim 1, wherein the host cells are haploid or diploid cells.

11. The method of claim 1, wherein the host cells contain a missense, a nonsense or a null mutation in at least one endogenous gene.

12. The method of claim 1, wherein the fluorescent protein is selected from the group consisting of a green, a blue, a red and a yellow fluorescent protein.

13. The method of claim 1, wherein the nucleotide sequence comprises only the promoter portion of the target gene.

14. The method of claim 1, wherein the nucleotide sequence comprises the promoter portion and other transcriptional regulatory elements of the target gene.

15. The method of claim 1, wherein the nucleotide sequence comprises the promoter portion, other transcriptional regulatory elements and at least a portion of the coding sequence of the target gene.

16. The method of claim 15, wherein the portion of the coding sequence of the target gene directs post-translational protein processing, modification, cellular location, transportation or metabolism of the protein encoded by the target gene.

17. The method of claim 1, wherein the nucleotide sequence comprises the promoter portion, other transcriptional regulatory elements and entire coding sequence of the target gene.

18. The method of claim 1, wherein the nucleotide sequence comprises the entire target gene.

19. The method of claim 1, wherein the reporter gene operatively linked to the nucleotide sequence is integrated into the genome of the host cell or is maintained episomally in the host cell.

20. The method of claim 19, wherein the reporter gene operatively linked to the nucleotide sequence is maintained episomally in a plasmid in the host cell.

21. The method of claim 1, wherein the first and second reporter genes are expressed at the same or different levels.

22. The method of claim 21, wherein the different expression levels of the first and second reporter genes are caused by the different cell ploidies or by different copy numbers of the reporter genes contained in the host cells.

23. The method of claim 1, wherein the nucleotide sequence is endogenous or exogenous to the host cell.

24. The method of claim 1, wherein the host cells used are yeast cells and the reporter genes are operatively linked to a nucleotide sequence of a non-yeast gene.

25. The method of claim 24, wherein the yeast cells are S. cerevisiae cells.

26. The method of claim 1, wherein the signal detection is real-time and/or in-situ detection.

27. The method of claim 1, wherein the signal detection is real-time and/or in-situ detection.

28. The method of claim 1, wherein the first host cell is treated, the third detectable signal detected in step c) moves toward the first detectable signal indicates that test substance enhances production of the target gene product controlled by the nucleotide sequence.

29. The method of claim 1, wherein the first host cell is treated, the third detectable signal detected in step c) moves toward the second detectable signal indicates that test substance inhibits production of said target gene product controlled by the nucleotide sequence.

30. The method of claim 1, wherein a plurality of treatments is screened for simultaneously.

31. The method of claim 1, wherein the treatment is a physical, chemical or biological treatment.

32. The method of claim 31, wherein the chemical treatment is effected by a test substance.

33. The method of claim 1, wherein a first plurality of host cells are constructed so that each of said first plurality of host cells contains a first reporter gene encoding a first flourescent protein operatively linked to a different nucleotide sequence of a plurality of nucleotide sequences, a second plurality of host cells are constructed so that each of said second plurality of host cells contains a second reporter gene encoding a second flourescent protein operatively linked to a different nucleotide sequence of said plurality of nucleotide sequences to which said first reporter gene is linked in said first plurality host cells, and the method is used to identify a modulator of production of a plurality of gene products.

34. A method of screening for a cellular target nucleotide sequence wherein said cellular target nucleotide sequence is regulated by treatment, which method comprises:

a) constructing a first host cell containing a first reporter gene operatively linked to a target nucleotide sequence and constructing a second host cell containing a second reporter gene encoding a second flourescent protein operatively linked to said target nucleotide sequence to which said first reporter gene is linked, wherein expression of said first reporter gene results in a first flourescently detectable signal, expression of said second reporter gene results in a second flourescently detectable signal, said first and second flourescently detectable signals are distinct from each other but are integratable, and wherein mixing of said first and second host cells are growth separately and then mixed to produce a third flourescently detectable signal distinct from said first and second flourescently detectable signals and detection of said third flourescently signal does not depend on the continued growth or viability of said first and second host cells;

b) detecting said third flourescently detectable signal from a mixture of said first and second host cells wherein neither type of said host cells is subjected to any desired treatment;

c) detecting said third flourescently detectable signal from a mixture of said first and second host cells wherein one and only one type of said host cells is subjected to a desired treatment prior to said mixing of said host cells; and d) comparing said third flourescently detectable signals detected in steps b) and c), whereby said third flourescently detectable signal detected in step b) differs from that detected in step c) identifies said target nucleotide sequence as amenable to regulation by said treatment.

wherein the method is performed in vitro.

35. The method of claim 34, wherein the treatment is a physical, chemical or biological treatment.

36. The method of claim 34, wherein the treatment is effected by a bioactive substance.

37. The method of claim 34, wherein the target nucleotide sequence is screened against a plurality of treatments simultaneously.

38. The method of claim 36, wherein the target nucleotide sequence is screened against a plurality of bioactive substances simultaneously.

39. The method of claim 34, wherein a first plurality of host cells are constructed so that each of said first plurality of host cells contains a first reporter gene encoding a first flourescent protein operatively linked to a different target nucleotide sequence of a plurality of target nucleotide sequences, a second plurality of host cells are constructed so that each of said second plurality of host cells contains a second reporter gene encoding a second flourescent protein operatively linked to a different target nucleotide sequence of said plurality of target nucleotide sequences to which said first reporter gene is linked in said first plurality of host cells, and the method is used to identify at least one target nucleotide sequence within said plurality of target nucleotide sequences that is amenable to regulation by said treatment.

40. The method of claim 39, wherein the plurality of target nucleotide sequences are endogenous to the host cells and the host cells are derived from a target organism.

41. The method of claim 40, wherein the plurality of target nucleotide sequences comprises an ensemble of the transcriptional regulatory elements of the target organism sufficient to model the transcriptional responsiveness of the target organism to the treatment.

42. The method of claim 41, wherein the ensemble comprises a majority of all different transcriptional regulatory elements of the target organism.

43. The method of claim 39, wherein a plurality of target nucleotide sequence is screened against a plurality of treatments simultaneously.

44. The method of claim 33, wherein the first plurality of host cells, the second plurality of host cells, or the mixture of the first and second plurality of host cells are placed and assayed in an array on a solid surface.

45. The method of claim 39, wherein the first plurality of host cells, the second plurality of host cells, or the mixture of the first and second plurality of host cells are placed and assayed in an array on a solid surface.

46. The method of claim 44, wherein the solid surface is selected from the group consisting of silicon, plastic, glass, polymer, ceramic, photoresist and rubber surface.

47. The method of claim 46, wherein the polymer is selected from the group consisting of cellulose, polyacrylamide, nylon, polystyrene, polyvinyl chloride and polypropylene.

48. The method of claim 46, wherein the silicon surface is a silicon dioxide or a silicon nitride surface.

49. The method of claim 44, wherein the array is made in a chip format.

50. The method of claim 44, wherein the solid surfaces are in the form of tubes, beads, discs, silicon chips, microplates, polyvinylidene difluoride (PVDF) membrane, nitrocellulose membrane, nylon membrane, other porous membrane, non-porous membrane, a plurality of polymeric pins, or a plurality of microtitre wells.

51. The method of claim 1, wherein more than two different reporter genes are used.

52. The method of claim 1, wherein the first and second reporter genes are used duplicatively as the reporter gene in a yeast two-hybrid system, and the method is used for screening for a treatment that modulates the protein-protein interaction assessable by said yeast two-hybrid system.

53. The method of claim 44, wherein the reporter genes used in the plurality of host cells further comprise a molecular tag capable of identifying the host cell containing the reporter gene.

54. The method of claim 45, wherein the reporter genes used in the plurality of host cells further comprise a molecular tag capable of identifying the host cell containing the reporter gene.

55. The method of claim 45, wherein the solid surface is selected from the group consisting of silicon, plastic, glass, polymer, ceramic, photoresist and rubber surface.

56. The method of claim 45, wherein the array is made in a chip format.

57. The method of claim 45, wherein the solid surfaces are in the form of tubes, beads, discs, silicon chips, microplates, polyvinylidene difluoride (PVDF) membrane, nitrocellulose membrane, nylon membrane, other porous membrane, non-porous membrane, a plurality of polymeric pins, or a plurality of microtitre wells.

58. The method of claim 34, wherein more than two different reporter genes are used.

59. The method of claim 1, wherein the first cell and the second host cell is the same cell.

60. The method of claim 1, wherein prior to or concurrently with measurement of the third detectable signal, the growth of the first and second host cells is stopped.

61. A method of screening for a modulator of production of a target gene product, which method comprises:

a) constructing a first host cell containing a first reporter gene encoding a first flourescent protein operatively linked to a nucleotide sequence comprising at least the promoter of a target gene and constructing a second host cell containing a second reporter gene encoding a second flourescent protein operatively linked to said nucleotide sequence to which said first reporter gene is linked, wherein expression of said first reporter gene results in a first flourescently detectable signal, expression of said second reporter gene results in a second flourescently detectable signal, said first and second flourescently detectable signals are distinct from each other but are integratable, and wherein said first and second host cells belong to the same genus, said first and second host cells are grown separately or together, and mixing of said first and second host cells results in a third flourescently detectable signal distinct from said first and second flourescently detectable signals;

b) detecting said third flourescently detectable signal from a mixture of said first and second host cells wherein neither type of said host cells is subjected to any desired treatment;

c) detecting said third flourescently detectable signal from a mixture of said first and second host cells wherein one and only one type of said host cells is subjected to a desired treatment prior to said mixing of said host cells; and d) comparing said third flourescently detectable signals detected in steps b) and c), whereby said third flourescently detectable signal detected in step b) differs from that detected in step c) identifies said treatment as a modulator of production of said target gene product, wherein the method is performed in vitro.

* * * * *